US00H002136H

(19) United States
(12) Statutory Invention Registration
Kulp et al.
(10) Reg. No.: US H2136 H
(43) Published: Dec. 6, 2005

(54) NUCLEIC ACIDS ENCODING G PROTEIN-COUPLED RECEPTORS

(75) Inventors: David C. Kulp, Albany, CA (US); Michael A. Siani-Rose, San Francisco, CA (US); Alan J. Williams, Albany, CA (US); Cyrus L. Harmon, Berkeley, CA (US)

(73) Assignee: Affymetrix, Inc., Santa Clara, CA (US)

(21) Appl. No.: 10/038,895

(22) Filed: Oct. 24, 2001

Related U.S. Application Data

(60) Provisional application No. 60/244,082, filed on Oct. 26, 2000.

(51) Int. Cl.[7] ..... C12P 21/06

(52) U.S. Cl. ..... 435/69.01; 530/350; 530/388.22; 435/7.2; 436/501; 710/360; 800/2

*Primary Examiner*—Aileen Felton

(74) *Attorney, Agent, or Firm*—Affymetrix, Inc.

(57) ABSTRACT

The present invention provides novel GPCR polynucleotides, GPCR polypeptides, gene delivery vehicles comprising and/or expressing the GPCR polynucleotides, antibodies and fragments capable of specifically binding to the GPCR polypeptides, and modulators of the GPCR. Also provided by the invention are host cells, transgenic organisms comprising the gene delivery vehicle of the present invention. Further provided are methods of using these compositions for diagnosis and treatment of GPCR associated diseases.

1 Claim, 10 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

SEQ ID NO:02

CTCTTGGCACCCACAGGTTCCTTGTTCCGAAACTGCACACAGGATGGCTGGTCAGAAACC
TTCCCCAGGCCTAATCTGGCCTGTGGCGTTAATGTGAACGACTCTTCCAACGAGAAGCGG
CACTCCTACCTGCTGAAGCTGAAAGTCATGTACACCGTGGGCTACAGCTCCTCCCTGGTC
ATGCTCCTGGTCGCCCTTGGCATCCTCTGTGCTTTCCGGAGGCTCCACTGCACTCGCAAC
TACATCCACATGCACCTGTTCGTGTCCTTCATCCTTCGTGCCCTGTCCAACTTCATCAAG
GACGCCGTGCTCTTCTCCTCAGATGATGTCACCTACTGCGATGCCCACAGGGCGGGCTGC
AAGCTGGTCATGGTGCTGTTC

Figure 1

Sequence Name:

GW.S.ctg16335-000003.31.0

Figure 1A SEQ ID NO:01

LLAPTGSLFRNCTQDGWSETFPRPNLACGVNVNDSSNEKRSYLLKLKVMYTVGYSSSLVM
LLVALGILCAFRRLHCTRNYIHMHLFVSFILRALSNFIKDAVLFSSDDVTYCDAHRGCKL
VMVLFXYCIMANYSWLLVEGSTFTHxLAISFFSERKYLQGFVAFGWGSPAIFVALWAIAR
HFLEDVGCWDINANASIWWIIRGPVILSILNFILFINILRILMRKLRTQETRGNEVSHYK
RLARSTLLLIPLFGIHYIVFAFSPEDAMEIQLFF

Figure 1B SEQ ID NO:02

CTCTTGGCACCCACAGGTTCCTTGTTCCGAAACTGCACACAGGATGGCTGGTCAGAAACC
TTCCCCAGGCCTAATCTGGCCTGTGGCGTTAATGTGAACGACTCTTCCAACGAGAAGCGG
CACTCCTACCTGCTGAAGCTGAAAGTCATGTACACCGTGGGCTACAGCTCCTCCCTGGTC
ATGCTCCTGGTCGCCCTTGGCATCCTCTGTGCTTTCCGGAGGCTCCACTGCACTCGCAAC
TACATCCACATGCACCTGTTCGTGTCCTTCATCCTTCGTGCCCTGTCCAACTTCATCAAG
GACGCCGTGCTCTTCTCCTCAGATGATGTCACCTACTGCGATGCCCACAGGGCGGGCTGC
AAGCTGGTCATGGTGCTGTTC

Figure 1C SEQ ID NO:03

TACTGCATCATGGCCAACTACTCCTGGCTGCTGGTGGAAGGCTCTACCTTCACACATNTC
CTCGCCATCTCCTTCTTCTCTGAAAGAAAGTACCTCCAGGGATTTGTGGCATTCGGATGG
GGTTCTCCAGCCATTTTTGTTGCTTTGTGGGCTATTGCCAGACACTTTCTGGAAGATGTT
GGGTGCTGGGACATCAATGCCAACGCATCCATCTGGTGGATCATTCGTGGTCCTGTGATC
CTCTCCATCCTGATTAATTTCATCCTTTTCATAAACATTCTAAGAATCCTGATGAGAAAA
CTTAGAACCCAAGAAACAAGAGGAAATGAAGTCAGCCATTATAAGCGCCTGGCCAGGTCC
ACTCTCCTGCTGATCCCCCTCTTTGGCATCCACTACATCGTCTTCGCCTTCTCCCCAGAG
GACGCTATGGAGATCCAGCTGTTTTTT

Figure 1D SEQ ID NO:04

CTCTTGGCACCCACAGGTTCCTTGTTCCGAAACTGCACACAGGATGGCTGGTCAGAAACC
TTCCCCAGGCCTAATCTGGCCTGTGGCGTTAATGTGAACGACTCTTCCAACGAGAAGCGG
CACTCCTACCTGCTGAAGCTGAAAGTCATGTACACCGTGGGCTACAGCTCCTCCCTGGTC
ATGCTCCTGGTCGCCCTTGGCATCCTCTGTGCTTTCCGGAGGCTCCACTGCACTCGCAAC
TACATCCACATGCACCTGTTCGTGTCCTTCATCCTTCGTGCCCTGTCCAACTTCATCAAG
GACGCCGTGCTCTTCTCCTCAGATGATGTCACCTACTGCGATGCCCACAGGGCGGGCTGC
AAGCTGGTCATGGTGCTGTTC
TACTGCATCATGGCCAACTACTCCTGGCTGCTGGTGGAAGGCTCTACCTTCACACATNTC
CTCGCCATCTCCTTCTTCTCTGAAAGAAAGTACCTCCAGGGATTTGTGGCATTCGGATGG
GGTTCTCCAGCCATTTTTGTTGCTTTGTGGGCTATTGCCAGACACTTTCTGGAAGATGTT
GGGTGCTGGGACATCAATGCCAACGCATCCATCTGGTGGATCATTCGTGGTCCTGTGATC
CTCTCCATCCTGATTAATTTCATCCTTTTCATAAACATTCTAAGAATCCTGATGAGAAAA
CTTAGAACCCAAGAAACAAGAGGAAATGAAGTCAGCCATTATAAGCGCCTGGCCAGGTCC
ACTCTCCTGCTGATCCCCCTCTTTGGCATCCACTACATCGTCTTCGCCTTCTCCCCAGAG
GACGCTATGGAGATCCAGCTGTTTTTT

Figure 2

Sequence Name:

GW.S.ctg16490-000000.17.0

Figure 2A SEQ ID NO:05

PTFILFSFQPGDKRTKHICVYWEGSEGGHWSTEGCSHVHSNGSYTKCKCFHLSSFAVLVA
LAPKDPVLTVITQVGLTISLLCLFLAILTFLLCRPIQNTSTSLHLELSLCLFLAHLLFLT
GINRTEPELCSIIAGLLHFLYLACFTWMLLEGLHLFLTVRNLKVANYTSTGRFKKRFMYP
VGYGIPAVIIAVSAIVGPQNYGTFTHCWLKLDKGFIWSFMGPVAVIILNLVFYFQVLWIL
RSKLSSLNKEVSTIQDTRVMTFKAISQLFILGCSWGLGFFMVEEVGKTIGSIIAYSFTII
NTLQGVLLFVVHCLLNRQVR

Figure 2B SEQ ID NO:06

CCCACTTTCATACTATTCTCTTTCCAGCCTGGTGACAAGAGAACAAAACATATCTGTGTC
TACTGGGAGGGATCAGAGGGAGGCCACTGGTCCACGGAGGGCTGCTCTCATGTGCACAGC
AACGGTTCTTACACCAAATGCAAGTGCTTCCATCTGTCCAGCTTTGCCGTCCTCGTGGCT
CTTGCCCCCAAGGAGGACCCTGTGCTGACCGTGATCACCCAGGTGGGGCTGACCATCTCT
CTGCTGTGCCTCTTCCTGGCCATCCTCACCTTCCTCCTGTGCCGGCCCATCCAGAACACC
AGCACCTCCCTCCATCTAGAGCTCTCCCTCTGCCTCTTCCTGGCCCACCTCCTGTTCCTG
ACGGGCATCAACAGAACTGAGCCTGAGGTGCTGTGCTCCATCATTGCAGGGCTGCTGCAC
TTCCTCTACCTGGCTTGCTTCACCTGGATGCTCCTGGAAGGGCTGCACCTCTTCCTCACC
GTCAGGAACCTCAAGGTGGCCAACTACACCAGCACGGGCAGATTCAAGAAGAGGTTCATG
TACCCTGTAGGCTACGGGATCCCAGCTGTGATTATTGCTGTGTCAGCAATAGTTGGACCC
CAGAATTATGGAACATTTACTCACTGTTGGCTCAAGCTTGATAAAGGATTCATCTGGAGC
TTCATGGGGCCAGTAGCAGTCATTATCTTGATAAACCTGGTGTTCTACTTCCAAGTTCTG
TGGATTTTGAGAAGCAAACTTTCCTCCCTCAATAAAGAAGTTTCCACCATTCAGGACACC
AGAGTCATGACATTTAAAGCCATTTCTCAGCTATTTATCCTGGGCTGTTCTTGGGGCCTT
GGTTTTTTTATGGTTGAAGAAGTAGGGAAGACGATTGGATCAATCATTGCATACTCATTC
ACCATCATCAACACCCTTCAGGGAGTGTTGCTCTTTGTGGTACACTGTCTCCTTAATCGC
CAGGTAAGG

Figure 3

Sequence Name:

GW.S.ctg13100-000000.33.0

Figure 3A SEQ ID NO:07

QHSDAVHDLLLDVITWVGILLSLVCLLICIFTFCFFRGLQSDRNTIHKNLCISLFVAELL
FLIGINRTDQPACAVFAALLHFFFLAAFTWMFLEGVQLYIMLVEVFESEHSRRKYFYLVG
YGMPALIVAVSAAVDYRSYGTDKVCWLRLDTYFIWSFIGPATLIIMNVIFLGIALYKMFH
HTAILKPESGCLDNIKLKINIPIIKSIYIYMYICMCV

Figure 3B SEQ ID NO:08

CAGCACAGTGATGCGGTCCATGACCTCCTTCTGGATGTGATCACGTGGGTTGGAATTTTG
CTGTCCCTTGTTTGTCTCCTGATTTGCATCTTCACATTTTGCTTTTTCCGGGGGCTCCAG
AGTGACCGTAACACCATCCACAAGAACCTCTGCATCAGTCTCTTTGTAGCAGAGCTGCTC
TTCCTGATTGGGATCAACCGAACTGACCAACCAATTGCCTGTGCTGTTTTCGCTGCCCTG
TTACATTTCTTCTTCTTGGCTGCCTTCACCTGGATGTTCCTGGAGGGGGTGCAGCTTTAT
ATCATGCTGGTGGAGGTTTTTGAGAGTGAACATTCACGTAGGAAATACTTTTATCTGGTC
GGCTATGGGATGCCTGCACTCATTGTGGCTGTGTCAGCTGCAGTAGACTACAGGAGTTAT
GGAACAGATAAAGTATGTTGGCTCCGACTTGACACCTACTTCATTTGGAGTTTTATAGGA
CCAGCAACTTTGATAATTATGCTTAATGTAATCTTCCTTGGGATTGCTTTATATAAAATG
TTTCATCATACTGCTATACTGAAACCTGAATCAGGCTGTCTTGATAACATCAAGTTAAAA
ATTAATATTCCAATTATAAAATCTATTTATATCTATATGTATATATGCATGTGTGTG

Figure 4

Sequence Name:

GW.A.ctg12444-000001.0.2

Figure 4A SEQ ID NO:09

GNVAVAFVYYKSIGPLLSSSDNFLLKPQNYDNSEEEERVISSVISVSMSSNPPTLYELEK
ITFTLSHRKTDRYRSLCAFWNYSPDTMNGSWSSEGCELTYSNETHTSCRCNHLTHFAILM
SSGPSIIKDYNILTRITQLGIIISLICLAICIFTFWFFSEIQSTRTTIHKNLCCSLFLAE
LVFLVGINTNTNKFCSIIAGLLHYFFLAAFAWMCIEGIHLYLIVVGVIYNKGFLHKNFYI
FGYLSPAVVVGFSAALGYRYYGTTKVCWLSTENNFIWSFIGPACLIILVCIYKIVITIQK
SDDH

Figure 4B SEQ ID NO:10

GGCAATGTTGCAGTTGCATTTGTATATTATAAGAGTATTGGTCCTTTGCTTTCATCATCT
GACAACTTCTTATTGAAACCTCAAAATTATGATAATTCTGAAGAGGAGGAAAGAGTCATA
TCTTCAGTAATTTCAGTCTCAATGAGCTCAAACCCACCCACATTATATGAACTTGAAAAA
ATAACATTTACATTAAGTCATCGAAAGGTCACAGATAGGTATAGGAGTCTATGTGCATTT
TGGAATTACTCACCTGATACCATGAATGGCAGCTGGTCTTCAGAGGGCTGTGAGCTGACA
TACTCAAATGAGACCCACACCTCATGCCGCTGTAATCACCTGACACATTTTGCAATTTTG
ATGTCCTCTGGTCCTTCCATTGGTATTAAAGATTATAATATTCTTACAAGGATCACTCAA
CTAGGAATAATTATTTCACTGATTTGTCTTGCCATATGCATTTTTACCTTCTGGTTCTTC
AGTGAAATTCAAAGCACCAGGACAACAATTCACAAAAATCTTTGCTGTAGCCTATTTCTT
GCTGAACTTGTTTTTCTTGTTGGGATCAATACAAATACTAATAAGCTCTTCTGTTCAATC
ATTGCCGGACTGCTACACTACTTCTTTTTAGCTGCTTTTGCATGGATGTGCATTGAAGGC
ATACATCTCTATCTCATTGTTGTGGGTGTCATCTACAACAAGGGATTTTTGCACAAGAAT
TTTTATATCTTTGGCTATCTAAGCCCAGCCGTGGTAGTTGGATTTTCGGCAGCACTAGGA
TACAGATATTATGGCACAACCAAAGTATGTTGGCTTAGCACCGAAAACAACTTTATTTGG
AGTTTTATAGGACCAGCATGCCTAATCATTCTTGTATGTATATATAAAATTGTTATTACA
ATTCAAAAAAGTGATGATCAT

Figure 5

Sequence Name:

GW.S.ctg12789-000004.100.0

Figure 5A SEQ ID NO:11

GAWATTGCSVAALYLDSTACFCNHSTSFAILLQIYEVQGPEEESLLRTLSFVGCGVSFCA
LTTTFLLFLVAGVPKSERTTVHKNLTFSLASAEGFLMTSEWAKANEACVAVTVAMHFLFL
VAFSWMLVEGLLLWRKVVAVSMHPGPGMRLYHATGWGVPVGIVAVTLAMLPHDYVAPGHC
WLNVHTNAIWAFVGPVLFVLTVS

Figure 5B SEQ ID NO:12

GGTGCCTGGGCCACCACAGGCTGCTCCGTGGCTGCCCTGTACCTGGACTCCACCGCCTGC
TTCTGCAACCACAGCACCAGCTTTGCCATCCTGCTGCAAATCTATGAAGTACAGAGAGGC
CCTGAGGAGGAGTCGCTGCTGAGGACTCTGTCATTTGTGGGCTGTGGCGTGTCCTTCTGC
GCCCTCACCACCACCTTCTTGCTCTTCCTGGTGGCCGGGGTCCCCAAGTCAGAGCGAACC
ACAGTCCACAAGAACCTCACCTTCTCCCTGGCCTCTGCCGAGGGCTTCCTCATGACCAGC
GAGTGGGCCAAGGCCAATGAGGTGGCATGTGTGGCTGTCACAGTCGCAATGCACTTCCTC
TTTCTGGTGGCATTCTCCTGGATGCTGGTGGAGGGGCTGCTGCTGTGGAGGAAGGTGGTA
GCTGTGAGCATGCACCCGGGCCCAGGCATGCGGCTCTACCACGCCACAGGCTGGGGCGTG
CCTGTGGGCATCGTGGCGGTCACCCTGGCCATGCTCCCCCATGACTACGTGGCCCCCGGA
CATTGCTGGCTCAATGTGCACACAAATGCCATCTGGGCCTTCGTGGGGCCTGTGCTCTTC
GTGCTGACTGTGAGC

*Figure 6*

Sequence Name:

GW.A.ctg12776-000000.33.0

Figure 6A SEQ ID NO:13

MKSPRRTTLCLMFIVIYSSKAALNWNYESTIHPLLHEHEPAGEEALRQKRAVATKSPTAE
EYTVNIEISFENASFLDPIKAYLNSLSFPIHGNNTDQITDILSINVTTVCRPAGNEIWCS
CETGYGWPRERCLHNLICQERDVFLPGHHCSCLKELPPNGPFCLLQEDVTLNMRVRLNVG
FQEDLMNTSSALYRSYKTDLETARKGYGILPGFKGVTVTGFKSGSVVVTYEVKTTPPSLE
LIHKANEQVVQSLNQTYKMDYNSFQAVTINESNFFVTPEIIFEGDTVSLVCEKEVLSSNV
SWRYEEQQLEIQNSSRFSIYTALFNNMTSVSKLTIHNITPGDAGEYVCKLILDIFEYECK
KKIDVMPIQILANEEMKVMCDNNPVSLNCCSQGNVNWSKVEWKQEGKINIPGTPETDIDS
SCSRYTLKADGTQCPSGSSGTTVIYTCEFISAYGARGSANIKVTFISVANLTITPDPISV
SEGQNFSIKCISDVSNYDEVYWNTSAGIKIYQRFYTTRRYLDGAESVLTVKTSTREWNGT
YHCIFRYKNSYSIATKDVIVHPLPLKLNIMVDPLEATVSCSGSHHIKCCIEEDGDYKVTF
HTGSSSLPAAKEVNKKQVCYKHNFNASSVSWCSKTVDVCCHFTNAANNSVWSPSMKLNLV
PGENITCQDPVIGVGEPGKVIQKLCRFSNVPSSPESPIGGTITYKCVGSQWEEKRNDCIS
APINSLLQMAKLIKSPSQDEMLPTYLKDLSISIDKAEHEISSSPGSLGAIINILDLLSTV
PTQVNSEMMTVLSTVNVILGKPVLNTWKVLQQQWTNQSSQLLHSVERFSQALQSGDSPPL
SFSQTNVQMSSMVIKSSHPETYQQRFVFPYFDLWGNVVIDKSYLENLQSDSSIVTMAFPT
LQAILAQDIQENNFAESLVMTTTVSHNTTMPFRISMTFKNNSPSGGETKCVFWNFRLANN
TGGWDSSGCYVEEGDGDNVTCICDHLTSFSILMSPDSPDPSSLLGILLDIISYVGVGFSI
LSLAACLVVEAVVWKSVTKNRTSYMRHTCIVNIAASLLVANTWFIVVAAIQDNRYILCKT
ACVAATFFIHFFYLSVFFWMLTLGLMLFYRLVFILHETSRSTQKAIAFCLGYGCPLAISV
ITLGATQPREVYTRKNVCWLNWEDTKALLAFAIPALIIVVVNITITIVVITKILRPSIGD
KPCKQEKSSLFQISKSIGVLTPLLGLTWGFGLTTVFPGTNLVFHIIFAILNVFQLFILLF
GCLWDLKQEALLNKFSLSRWSSQHSKTSLGSSTPVFSMSSPISRRFNNLFGKTGTYNVST
PEATSSSLENSSSASSLLN

Figure 6B SEQ ID NO:14

ATGAAATCCCCAAGGAGAACCACTTTGTGCCTCATGTTTATTGTGATTTATTCTTCCAAA
GCTGCACTGAACTGGAATTACGAGTCTACTATTCATCCTTTGAGTCTTCATGAACATGAA
CCAGCTGGTGAAGAGGCACTGAGGCAAAAACGAGCCGTTGCCACAAAAAGTCCTACGGCT
GAAGAATACACTGTTAATATTGAGATCAGTTTTGAAAATGCATCCTTCCTGGATCCTATC
AAAGCCTACTTGAACAGCCTCAGTTTTCCAATTCATGGGAATAACACTGACCAAATTACC
GACATTTTGAGCATAAATGTGACAACAGTCTGCAGACCTGCTGGAAATGAAATCTGGTGC
TCCTGCGAGACAGGTTATGGGTGGCCTCGGGAAAGGTGTCTTCACAATCTCATTTGTCAA
GAGCGTGACGTCTTCCTCCCAGGGCACCATTGCAGTTGCCTTAAAGAACTGCCTCCCAAT
GGACCTTTTTGCCTGCTTCAGGAAGATGTTACCCTGAACATGAGAGTCAGACTAAATGTA
GGCTTTCAAGAAGACCTCATGAACACTTCCTCCGCCCTCTATAGGTCCTACAAGACCGAC
TTGGAAACAGCGTTCCGGAAGGGTTACGGAATTTTACCAGGCTTCAAGGGCGTGACTGTG
ACAGGGTTCAAGTCTGGAAGTGTGGTTGTGACATATGAAGTCAAGACTACACCACCATCA
CTTGAGTTAATACATAAAGCCAATGAACAAGTTGTACAGAGCCTCAATCAGACCTACAAA
ATGGACTACAACTCCTTTCAAGCAGTTACTATCAATGAAAGCAATTTCTTTGTCACACCA
GAAATCATCTTTGAAGGGGACACAGTCAGTCTGGTGTGTGAAAAGGAAGTTTTGTCCTCC
AATGTGTCTTGGCGCTATGAAGAACAGCAGTTGGAAATCCAGAACAGCAGCAGATTCTCG
ATTTACACCGCACTTTTCAACAACATGACTTCGGTGTCCAAGCTCACCATCCACAACATC
ACTCCAGGTGATGCAGGTGAATATGTTTGCAAACTGATATTAGACATTTTTGAATATGAG
TGCAAGAAGAAAATAGATGTTATGCCCATCCAAATTTTGGCAAATGAAGAAATGAAGGTG
ATGTGCGACAACAATCCTGTATCTTTGAACTGCTGCAGTCAGGGTAATGTTAATTGGAGC
AAAGTAGAATGGAAGCAGGAAGGAAAAATAAATATTCCAGGAACCCCTGAGACAGACATA
GATTCTAGCTGCAGCAGATACACCCTCAAGGCTGATGGAACCCAGTGCCCAAGCGGGTCG

TCTGGAACAACAGTCATCTACACTTGTGAGTTCATCAGTGCCTATGGAGCCAGAGGCAGT
GCAAACATAAAAGTGACATTCATCTCTGTGGCCAATCTAACAATAACCCCGGACCCAATT
TCTGTTTCTGAGGGACAAAACTTTTCTATAAAATGCATCAGTGATGTGAGTAACTATGAT
GAGGTTTATTGGAACACTTCTGCTGGAATTAAAATATACCAAAGATTTTATACCACGAGG
AGGTATCTTGATGGAGCAGAATCAGTACTGACAGTCAAGACCTCGACCAGGGAGTGGAAT
GGAACCTATCACTGCATATTTAGATATAAGAATTCATACAGTATTGCAACCAAAGACGTC
ATTGTTCACCCGCTGCCTCTAAAGCTGAACATCATGGTTGATCCTTTGGAAGCTACTGTT
TCATGCAGTGGTTCCCATCACATCAAGTGCTGCATAGAGGAGGATGGAGACTACAAAGTT
ACTTTCCATACGGGTTCCTCATCCCTTCCTGCTGCAAAAGAAGTTAACAAAAAACAAGTG
TGCTACAAACACAATTTCAATGCAAGCTCAGTTTCCTGGTGTTCAAAAACTGTTGATGTG
TGTTGTCACTTTACCAATGCTGCTAATAATTCAGTCTGGAGCCCATCTATGAAGCTGAAT
CTGGTTCCTGGGGAAAACATCACATGCCAGGATCCCGTAATAGGTGTCGGAGAGCCGGGG
AAAGTCATCCAGAAGCTATGCCGGTTCTCAAACGTTCCCAGCAGCCCTGAGAGTCCCATT
GGCGGGACCATCACTTACAAATGTGTAGGCTCCCAGTGGGAGGAGAAGAGAAATGACTGC
ATCTCTGCCCCAATAAACAGTCTGCTCCAGATGGCTAAGGCTTTGATCAAGAGCCCCTCT
CAGGATGAGATGCTCCCTACATACCTGAAGGATCTTTCTATTAGCATAGACAAAGCGGAA
CATGAAATCAGCTCTTCTCCTGGGAGTCTGGGAGCCATTATTAACATCCTTGATCTGCTC
TCAACAGTTCCAACCCAAGTAAATTCAGAAATGATGACGCACGTGCTCTCTACGGTTAAT
GTCATCCTTGGCAAGCCCGTCTTGAACACCTGGAAGGTTTTACAACAGCAATGGACCAAT
CAGAGTTCACAGCTACTACATTCAGTGGAAAGATTTTCCCAAGCATTACAGTCGGGAGAT
AGCCCTCCTTTGTCCTTCTCCCAAACTAATGTGCAGATGAGCAGCATGGTAATCAAGTCC
AGCCACCCAGAAACCTATCAACAGAGGTTTGTTTTCCCATACTTTGACCTCTGGGGCAAT
GTGGTCATTGACAAGAGCTATCTAGAAAACTTGCAGTCGGATTCGTCTATTGTCACCATG
GCTTTCCCAACTCTCCAAGCCATCCTTGCCCAGGATATCCAGGAAAATAACTTTGCAGAG
AGCTTAGTGATGACAACCACTGTCAGCCACAATACAACTATGCCATTCAGGATTTCAATG
ACTTTTAAGAACAATAGCCCTTCAGGCGGCGAAACGAAGTGTGTCTTCTGGAACTTCAGG
CTTGCCAACAACACAGGGGGGTGGGACAGCAGTGGGTGCTATGTAGAAGAAGGTGATGGG
GACAATGTCACCTGTATCTGTGACCACCTAACATCATTCTCCATCCTCATGTCCCCTGAC
TCCCCAGATCCTAGTTCTCTCCTGGGAATACTCCTGGATATTATTTCTTATGTTGGGGTG
GGCTTTTCCATCTTGAGCTTGGCAGCCTGTCTAGTTGTGGAAGCTGTGGTGTGGAAATCG
GTGACCAAGAACCGGACTTCTTATATGCGCCACACCTGCATAGTGAATATCGCTGCCTCC
CTTCTGGTCGCCAACACCTGGTTCATTGTGGTCGCTGCCATCCAGGACAATCGCTACATA
CTCTGCAAGACAGCCTGTGTGGCTGCCACCTTCTTCATCCACTTCTTCTACCTCAGCGTC
TTCTTCTGGATGCTGACACTGGGCCTCATGCTGTTCTATCGCCTGGTTTTCATTCTGCAT
GAAACAAGCAGGTCCACTCAGAAAGCCATTGCCTTCTGTCTTGGCTATGGCTGCCCACTT
GCCATCTCGGTCATCACGCTGGGAGCCACCCAGCCCCGGGAAGTCTATACGAGGAAGAAT
GTCTGTTGGCTCAACTGGGAGGACACCAAGGCCCTGCTGGCTTTCGCCATCCCAGCACTG
ATCATTGTGGTGGTGAACATAACCATCACTATTGTGGTCATCACCAAGATCCTGAGGCCT
TCCATTGGAGACAAGCCATGCAAGCAGGAGAAGAGCAGCCTGTTTCAGATCAGCAAGAGC
ATTGGGGTCCTCACACCACTCTTGGGCCTCACTTGGGGTTTTGGTCTCACCACTGTGTTC
CCAGGGACCAACCTTGTGTTCCATATCATATTTGCCATCCTCAATGTCTTCCAGGGATTA
TTCATTTTACTCTTTGGATGCCTCTGGGATCTGAAGGTACAGGAAGCTTTGCTGAATAAG
TTTTCATTGTCGAGATGGTCTTCACAGCACTCAAAGTCAACATCCCTGGGTTCATCCACA
CCTGTGTTTTCTATGAGTTCTCCAATATCAAGGAGATTTAACAATTTGTTTGGTAAAACA
GGAACGTATAATGTTTCCACCCCAGAAGCAACCAGCTCATCCCTGGAAAACTCATCCAGT
GCTTCTTCGTTGCTCAAC

FIGURE 6B (Continuation)

Figure 7

Sequence Name:

GW.S.ctg12776-000000.175.0

Figure 7A SEQ ID NO:15

ILNSKSISNWTFIRDRNSSYILLHSVNSFARRLFIDNIPVDISDVFIHTMGTTISGDNIG
KNFTFSMRINDTSNEVTGRVLISRDELRKVPSPSQVISIAFPTIGAILEASLLENVTVNG
LVLSAILPKELKRISLIFEKISKSEERRTQCVGWHSVENRWDQQACKMIQENSQQAVCKC
RPSKLFTSFSILMSPHILESLILTYITYVGLGISICSLILCLSIEVLVWSQVTKTEITYL
RHVCIVNIAATLLMADVWFIVASFLSGPITHHKGCVAATFFVHFFYLSVFFWMLAKALLI
LYGIMIVFHTLPKSVLVASLFSVGYGCPLAIAAITVAATEPGKGYLRPEICWLNWDMTKA
LLAFVIPALAIVVVNLITVTLVIVKTQRAAIGNSMFQEVRAIVRISKNIAILTPLLGLTW
GFGVATVIDDRSLAFHIIFSLLNAFQFFILVFGTILDPKV

Figure 7B SEQ ID NO:16

ATTCTTAACAGCAAAAGCATCTCCAACTGGACTTTCATTCGTGACAGAAACAGCAGCTAT
ATCCTGCTACATTCAGTCAACTCCTTTGCAAGAAGGCTATTCATAGATAACATCCCTGTT
GACATATCAGATGTCTTCATTCATACTATGGGCACCACCATATCTGGAGATAACATTGGA
AAAAATTTCACTTTTTCTATGAGAATTAATGACACCAGCAATGAAGTCACTGGGAGAGTG
TTGATCAGCAGAGATGAACTTCGGAAGGTGCCTTCCCCTTCTCAGGTCATCAGCATTGCA
TTTCCAACTATTGGGGCTATTTTGGAAGCCAGTCTTTTGGAAAATGTTACTGTAAATGGG
CTTGTCCTGTCTGCCATTTTGCCCAAGGAACTTAAAAGAATCTCACTGATTTTTGAAAAG
ATCAGCAAGTCAGAGGAGAGGAGGACACAGTGTGTTGGCTGGCACTCTGTGGAGAACAGA
TGGGACCAGCAGGCCTGCAAAATGATTCAAGAAAACTCCCAGCAAGCTGTTTGCAAATGT
AGGCCAAGCAAATTGTTTACCTCTTTCTCAATTCTTATGTCACCTCACATCTTAGAGAGT
CTGATTCTGACTTACATCACATATGTAGGCCTGGGCATTTCTATTTGCAGCCTGATCCTT
TGCTTGTCCATTGAGGTCCTAGTCTGGAGCCAAGTGACAAAGACAGAGATCACCTATTTA
CGCCATGTGTGCATTGTTAACATTGCAGCCACTTTGCTGATGGCAGATGTGTGGTTCATT
GTGGCTTCCTTTCTTAGTGGCCCAATAACACACCACAAGGGATGTGTGGCAGCCACATTT
TTTGTTCATTTCTTTTACCTTTCTGTATTTTTCTGGATGCTTGCCAAGGCACTCCTTATC
CTCTATGGAATCATGATTGTTTTCCATACCTTGCCCAAGTCAGTCCTGGTGGCATCTCTG
TTTTCAGTGGGCTATGGATGCCCTTTGGCCATTGCTGCCATCACTGTTGCTGCCACTGAA
CCTGGCAAAGGCTATCTACGACCTGAGATCTGCTGGCTCAACTGGGACATGACCAAAGCC
CTCCTGGCCTTCGTGATCCCAGCTTTGGCCATCGTGGTAGTAAACCTGATCACAGTCACA
CTGGTGATTGTCAAGACCCAGCGAGCTGCCATTGGCAATTCCATGTTCCAGGAAGTGAGA
GCCATTGTGAGAATCAGCAAGAACATCGCCATCCTCACACCACTTCTGGGACTGACCTGG
GGATTTGGAGTAGCCACTGTCATCGATGACAGATCCCTGGCCTTCCACATTATCTTCTCC
CTGCTCAATGCATTCCAGGGTTTCTTCATCCTAGTGTTTGGAACCATCCTGGATCCAAAG
GTA

Figure 8

Sequence Name:

GW.S.ctg16790-000000.13.0

Figure 8A SEQ ID NO:17

GTTGDWSSEGCSTEVRPEGTVCCCDHLTFFALLLPTLDQSTVHILTRISQAGCGVSMIFL
AFTIILYAFLRLSRERFKSEDAPKIHVALGGSLFLLNLAFLVNVGSGSKGSDAACWARGA
VFHYFLLCAFTWMGLEAFHLYLLAVRVFNTYFGHYFLKLSLVGWGLPALMVIGTGSANSY
GLYTIRDRENRTSLELCWFREGTTMYALYITVHGYFLITFLFGMVVLALVVWKIFTLSRA
TAVKERGKNRKKVLTILLGLSSLVGVTWGLAIFTPLGLSTVYIFALFNSLQVDFYILIFY

Figure 8B SEQ ID NO:18

GGGACCACTGGAGACTGGTCTTCTGAGGGCTGCTCCACGGAGGTCAGACCTGAGGGGACC
GTGTGCTGCTGTGACCACCTGACCTTTTTCGCCCTGCTCCTGAGACCCACCTTGGACCAG
TCCACGGTGCATATCCTCACACGCATCTCCCAGGCGGGCTGTGGGGTCTCCATGATCTTC
CTGGCCTTCACCATTATTCTTTATGCCTTTCTGAGGCTTTCCCGGGAGAGGTTCAAGTCA
GAAGATGCCCCAAAGATCCACGTGGCCCTGGGTGGCAGCCTGTTCCTCCTGAATCTGGCC
TTCTTGGTCAATGTGGGGAGTGGCTCAAAGGGGTCTGATGCTGCCTGCTGGGCCCGGGGG
GCTGTCTTCCACTACTTCCTGCTCTGTGCCTTCACCTGGATGGGCCTTGAAGCCTTCCAC
CTCTACCTGCTCGCTGTCAGGGTCTTCAACACCTACTTCGGGCACTACTTCCTGAAGCTG
AGCCTGGTGGGCTGGGGCCTGCCCGCCCTGATGGTCATCGGCACTGGGAGTGCCAACAGC
TACGGCCTCTACACCATCCGTGATAGGGAGAACCGCACCTCTCTGGAGCTATGCTGGTTC
CGTGAAGGGACAACCATGTACGCCCTCTATATCACCGTCCACGGCTACTTCCTCATCACC
TTCCTCTTTGGCATGGTGGTCCTGGCCCTGGTGGTCTGGAAGATCTTCACCCTGTCCCGT
GCTACAGCGGTCAAGGAGCGGGGGAAGAACCGGAAGAAGGTGCTCACCCTGCTGGGCCTC
TCGAGCCTGGTGGGTGTGACATGGGGGTTGGCCATCTTCACCCCGTTGGGCCTCTCCACC
GTCTACATCTTTGCACTTTTCAACTCCTTGCAAGTTGATTTTTACATATTGATCTTCTAT

Figure 9

Sequence Name:

GW.S.ctg12776-000000.172.0

Figure 9A SEQ ID NO:19

NHILDTAAISNWAFIPNKNASSDLLQSVNLFARQLHIHNNSENIVNELFIQTKGFHINHN
TSEKSLNFSMSMNNTTEDILGMVQIPRQELRKLWPNASQAISIAFPTLGAILREAHLQNV
SLPRQVNGLVLSVVLPERLQEIILTFEKINKTRNARAQCVGWHSKKRRWDEKACQMMLDI
RNEVKCRCNYTSVVMSFSILMSSKSMTDKVLDYITCIGLSVSILSLVLCLIIEATVWSRV
VVTEISYMRHVCIVNIAVSLLTANVWFIIGSHFNIKAQDYNMCVAVTFFSHFFYLSLFFW
MLFKALLIIYGILVIFRRMMKSRMMVIGFAIGYGCPLIIAVTTVAITEPEKGYIRPEACW
LNWDNTKALXAFAIPAFVIVAVNLIVVLVVAVNTQRPSIGSSKSQDVVIIMRISKNVAIL
TPLLGLTWGFGIATLIEGTSLTFHIIFALLNAFQFFILLFGTIMDHKV

Figure 9B SEQ ID NO:20

AACCACATCCTCGACACAGCAGCCATTTCAAACTGGGCTTTCATTCCCAACAAAAATGCC
AGCTCGGATTTGTTGCAGTCAGTGAATTTGTTTGCCAGACAACTCCACATCCACAATAAT
TCTGAGAACATTGTGAATGAACTCTTCATTCAGACAAAAGGGTTTCACATCAACCATAAT
ACCTCAGAGAAAAGCCTCAATTTCTCCATGAGCATGAACAATACCACAGAAGATATCTTA
GGAATGGTACAGATTCCCAGGCAAGAGCTAAGGAAGCTGTGGCCAAATGCATCCCAAGCC
ATTAGCATAGCTTTCCCAACCTTGGGGGCTATCCTGAGAGAAGCCCACTTGCAAAATGTG
AGTCTTCCCAGACAGGTAAATGGTCTGGTGCTATCAGTGGTTTTACCAGAAAGGTTGCAA
GAAATCATACTCACCTTCGAAAAGATCAATAAAACCCGCAATGCCAGAGCCCAGTGTGTT
GGCTGGCACTCCAAGAAAAGGAGATGGGATGAGAAAGCGTGCCAAATGATGTTGGATATC
AGGAACGAAGTGAAATGCCGCTGTAACTACACCAGTGTGGTGATGTCTTTTTCCATTCTC
ATGTCCTCCAAATCGATGACCGACAAAGTTCTGGACTACATCACCTGCATTGGGCTCAGC
GTCTCAATCCTAAGCTTGGTTCTTTGCCTGATCATTGAAGCCACAGTGTGGTCCCGGGTG
GTTGTGACGGAGATATCATACATGCGTCACGTGTGCATCGTGAATATAGCAGTGTCCCTT
CTGACTGCCAATGTGTGGTTTATCATAGGCTCTCACTTTAACATTAAGGCCCAGGACTAC
AACATGTGTGTTGCAGTGACATTTTTCAGCCACTTTTTCTACCTCTCTCTGTTTTTCTGG
ATGCTCTTCAAAGCATTGCTCATCATTTATGGAATATTGGTCATTTTCCGTAGGATGATG
AAGTCCCGAATGATGGTCATTGGCTTTGCCATTGGCTATGGGTGCCCATTGATCATTGCT
GTCACTACAGTTGCTATCACAGAGCCAGAGAAAGGCTACATAAGACCTGAGGCCTGTTGG
CTTAACTGGGACAATACCAAAGCCCTTTAAGCATTTGCCATCCCGGCGTTCGTCATTGTG
GCTGTAAATCTGATTGTGGTTTTGGTTGTTGCTGTCAACACTCAGAGGCCCTCTATTGGC
AGTTCCAAGTCTCAGGATGTGGTCATAATTATGAGGATCAGCAAAAATGTTGCCATCCTC
ACTCCACTGCTGGGACTGACCTGGGGTTTTGGAATAGCCACTCTCATAGAAGGCACTTCC
TTGACGTTCCATATAATTTTTGCCTTGCTCAATGCTTTCCAGGGTTTTTTCATCCTGCTG
TTTGGAACCATTATGGATCACAAGGTA

NUCLEIC ACIDS ENCODING G PROTEIN-COUPLED RECEPTORS

This application claims the priority of U.S. Provisional Application Ser. No. 60/244,082, filed on Oct. 26, 2000. The '082 application is incorporated herein by reference for all purposes.

TECHNICAL FIELD

This invention is in the field of genetic analysis. Specifically, the invention relates to the discovery, identification and characterization of nucleic acids that encode novel G-protein coupled receptors. The compositions and methods embodied in the present invention are particularly useful for diagnosis, prognoses, drug screening, and/or treatment of disorders that are associated with dysfunction of the G-protein coupled receptors.

BACKGROUND OF THE INVENTION

Cell surface receptors are molecules anchored on the cell plasma membrane. They constitute a large family of proteins, glycoproteins, polysaccharides and lipids, which serve not only as structural constituents of the plasma membrane, but more importantly as regulatory elements governing a variety of biological functions. Over the past decades, numerous cell surface receptors have been identified, cloned and found to play a pivotal role in the transduction of signals triggered by external stimuli such as growth factors and hormones that culminate in a wide range of cellular responses. Among them are cell division, apoptosis, differentiation, and motility.

G protein-coupled receptors (GPCRs) form a large family of related proteins. GPCRs are characterized as having a transmembrane domain consisting of seven putative spanning segments, an extracellular amino terminus with ligand binding sites, and an intracellular carboxyl terminus that is capable of interacting with heteromultimeric G-proteins to transduce downstream signals. GPCRs may be broadly divided into Gq, Gs and Gi types depending on the classes of heteromultimeric G-proteins they interact with. Generally, a heteromultimeric G-protein complex is comprised of $\alpha$, $\beta$, and $\gamma$ subunits. More than half of the GPCRs are either Gs or Gi type, as they appear to couple to the heterotrimeric G proteins Gs or Gi in which the $\alpha$ subunit is $\alpha_s$ or $\alpha_i$. Typically, activation of a GPCR by an agonist (i.e. a positive modulator such as a specific ligand) causes the GPCR to interact with and activate a particular class of heteromultimeric G protein. In the activated G protein, GDP bound to the a subunit is replaced with GTP followed by the dissociation of $\alpha_{GTP}$ from the $\beta\gamma$ dimer. The activated G protein subunits ($\alpha_{GTP}$ or free $\beta\gamma$) are then able to modulate downstream signal transduction events via other intracellular signaling molecules (see, e.g., E. J. Neer, Cell 80: 249–257, 1995).

Both Gs and Gi signal through the cyclic AMP (cAMP) pathway. In particular, Gs stimulates adenylyl cyclase, resulting in an increase in intracellular cAMP concentration, whereas Gi inhibits adenylyl cyclase, causing a decrease in intracellular cAMP level. A smaller number of GPCRs activate a phospholipase C (PLC) pathway by coupling with a distinct group of heterotrimeric G proteins, Gq in which the $\alpha$ subunit is $\alpha_q$. Phospholipase C hydrolyzes phosphoinositides to generate two classes of well-characterized second messengers, namely, diacylglycerol and inositol phosphates. Diacylglycerol activates certain protein kinase Cs (PKCs) and certain inositol phosphates stimulate the mobilization of calcium from intracellular stores.

Phosphorylation and lipidation (palmitylation or farnesylation) of cysteine residues have been shown to influence signal transduction of some GPCRs. Most G-protein coupled receptors contain potential phosphorylation sites within the third cytoplasmic loop and/or the carboxyl terminus. For several G-protein coupled receptors, such as the $\beta$-adrenoreceptor, phosphorylation by protein kinase A and/or specific receptor kinases mediates receptor desensitization.

In mammals, it is believed that more than 1000 genes encode GPCRs of one type or another. Of those, several hundred GPCRs are likely to be involved in various disease processes including but not limited to cardiovascular disorders, neurological and metabolic disorders, asthma, hyprecalcemia, hypertension, prostate hypertrophy and various forms of cancer. Over the past fifteen years, over 350 therapeutic agents targeting GPCRs have been successfully introduced onto the market. Clearly, GPCRs are important diagnostic and/or therapeutic targets. There thus remains a considerable need for identification and characterization of novel GPCRs.

SUMMARY OF THE INVENTION

A principal aspect of the present invention relates to the discovery, isolation and characterization of novel GPCR polynucleotides, which exhibit sequence homology with previously characterized GPCRs including receptors of:

HUMAN CALCITONIN [CALCR];
HUMAN CALCITONIN GENE-RELATED PEPTIDE TYPE 1 (CGRP TYPE 1) [CGRPR];
HUMAN CORTICOTROPIN RELEASING FACTOR 1 (CRF1) [CRHR1; CRHR; CRFR];
HUMAN CORTICOTROPIN RELEASING FACTOR 2 (CRF2) [CRHR2; CRF2R];
HUMAN GASTRIC INHIBITORY PEPTIDE (GIP-R) [GIPR];
HUMAN GLUCAGON (GL-R) [GCGR];
HUMAN GLUCAGON-LIKE PEPTIDE 1 (GLP-1-R) [GLPIR];
HUMAN GROWTH HORMONE-RELEASING HORMONE (GRFR) [GHRHR];
HUMAN PARATHYROID HORMONE/PARATHYROID HORMONE-RELATED PEPTIDE [PTHRI; PTHR];
PARATHYROID HORMONE (PTH2) [PTHR2];
PITUITARY ADENYLATE CYCLASE ACTIVATING POLYPEPTIDE TYPE I;
HUMAN SECRETIN (SCT-R) [SCTR];
HUMAN VASOACTIVE INTESTINAL POLYPEPTIDE 1 (VIP-R-1) [VIPR1];
HUMAN VASOACTIVE INTESTINAL POLYPEPTIDE 2 (VIP-R-2) (PACAP-R-3) [VIPR2];
HUMAN LEUCOCYTE ANTIGEN CD97 [CD97]; and
HUMAN CELL SURFACE GLYCOPROTEIN EMR1 [EMR1]. All of these genes generally fall under GPCR family 2B.

In one embodiment, the present invention provides an isolated GPCR polynucleotide comprising a nucleic acid sequence depicted in any one of the FIGS. 1B, 1C, 1D, 2B, 3B, 4B, 5B, 6B, 7B, 8B, and 9B. In one aspect of this embodiment, the isolated polynucleotide comprising a nucleic acid sequence selected from the group consisting of: (a) a nucleic acid sequence of at least 90 nucleotides that is essentially identical to a linear sequence of comparable length contained in the sequence shown in any one of the FIGS. 1B, 1C, 1D, 2B, 3B, 4B, 5B, 6B, 7B, 8B, and 9B; (b) a nucleic acid sequence of at least 90 nucleotides encoding a polypeptide that is essentially identical to a linear sequence of at least 30 amino acids contained in the sequence shown in any one of the FIGS. 1A, 2A, 3A, 4A, 5A, 6A, 7A, 8A and 9A; and (c) a complement of (a) or (b). In another aspect, the isolated polynucleotide encodes a polypeptide comprising an amino acid sequence that is essentially identical to a linear sequence of comparable length shown in any one of the 1A, 2A, 3A, 4A, 5A, 6A, 7A, 8A and 9A. In yet another aspect, the isolated polynucleotide encodes a polypeptide comprising an amino acid sequence essentially identical to the entire amino acid sequence shown in any one of the FIGS. 1A, 2A, 3A, 4A, 5A, 6A, 7A, 8A, and 9A. In still another aspect, the isolated polynucleotide encodes a polypeptide comprising the amino acid sequence shown in any one of the FIGS. 1A, 2A, 3A, 4A, 5A, 6A, 7A, 8A, and 9A. The polynucleotide of the present invention can code for the whole or domain(s) of the GPCR (e.g. the extracellular, transmembrane or cytoplasmic domain), or a mutant, fusion or a functional equivalent GPCR polypeptide. A preferred polynucleotide encodes one of the seven transmembrane regions of the GPCR. In a related aspect of this embodiment, the invention encompasses a method of diagnosing a pathogenic condition or susceptibility to a pathogenic condition that is associated with a genetic alteration in a GPCR polypeptide encoded by the claimed polynucleotide. The method comprises the steps of: (a) providing a biological sample of a subject containing nucleic acid molecules and/or polypeptides; (b) determining a genetic alteration associated with the GPCR; and (c) correlating the alteration with a pathogenic condition or susceptibility to a pathogenic condition.

In a separate embodiment, the invention provides GPCR polypeptides encoded by the isolated polynucleotides. In another embodiment, the invention provides antibodies and antigen-binding fragments that are capable of specifically binding to the GPCR or fragments thereof. Also encompassed by the invention are gene delivery vehicles comprising the isolated GPCR polynucleotides, genetically engineered host cells and transgenic organisms carrying the gene delivery vehicles. Such a host cell or transgenic organism may express GPCR or lack GPCR expression (e.g. "knockouts"). In a related aspect, the invention includes a recombinant method of producing a GPCR polypeptide that comprises culturing the genetically engineered host cell under conditions suitable for protein expression, and isolating the expressed polypeptide.

In another embodiment, this invention encompass modulators including agonists and antagonists of GPCR. Modulators can be small molecules, large molecules, mutant GPCR ligands that compete with native natural GPCR ligand, and antibodies, as well as nucleotide sequences that can be used to inhibit GPCR gene expression (e.g., antisense and ribozyme molecules, and gene or regulatory sequence replacement constructs) or to enhance GPCR gene expression (e.g., expression constructs that place the GPCR gene under the control of a strong promoter system).

In yet another embodiment, the present invention provides a method for identifying a modulator that regulates GPCR expression or GPCR activity. Measurable GPCR activities include but are not limited to stimulation or inhibition of phospholipase C and adenylyl cyclase, transient mobilization of $Ca^{2+}$ from intracellular stores, ion flux, and change of intracellular pH condition.

In still another embodiment, the invention encompasses pharmaceutical compositions used for the diagnosis, prognosis or treatment of GPCR associated diseases.

Also provided by the invention are kits comprising the GPCR polynucleotides and/or polypeptides encoded thereby.

Further provided by the invention is a computer readable medium having recorded thereon the GPCR polynucleotide sequence and/or encoded gene product that are disclosed herein. The computer readable medium can be (a) magnetic storage medium; (b) optical storage medium; (c) electrical storage medium; or (d) hybrid storage medium of (a), (b), (c) or (d).

BRIEF DESCRIPTION OF THE DRAWINGS

FIG. 1 depicts nucleotide and protein sequence of the GPCR gene designated GW.S.ctg16335-000003.31.0.

FIG. 2 depicts nucleotide and protein sequence of the GPCR gene designated GW.S.ctg16490-000000.17.0.

FIG. 3 depicts nucleotide and protein sequence of the GPCR gene designated S GW.S.ctg13100-000000.33.0.

FIG. 4 depicts nucleotide and protein sequence of the GPCR gene designated GW.A.ctg12444-000001.0.2.

FIG. 5 depicts nucleotide and protein sequence of the GPCR gene designated GW.S.ctg12789-000004.100.0.

FIG. 6 depicts nucleotide and protein sequence of the GPCR gene designated GW.A.ctg12776-000000.33.0.

FIG. 7 depicts nucleotide and protein sequence of the GPCR gene designated GW.S.ctg12776-000000.175.0.

FIG. 8 depicts nucleotide and protein sequence of the GPCR gene designated GW.S.ctg16790-000000.13.0.

FIG. 9 depicts nucleotide and protein sequence of the GPCR gene designated GW.S.ctg12776-000000.172.0.

FIG. 10 is a schematic representation of sequence alignments of existing and claimed GPCR sequences against the Hidden Markov Model constructed for the Family 2B subclass GPCRs.

MODE(S) FOR CARRYING OUT THE INVENTION

Throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

General Techniques:

The practice of the present invention will employ, unless otherwise indicated, conventional techniques of immunology, biochemistry, chemistry, molecular biology, microbiology, cell biology, genomics and recombinant DNA, which are within the skill of the art. See, e.g., Matthews, PLANT VIROLOGY, $3^{rd}$ edition (1991); Sambrook, Fritsch and Maniatis, MOLECULAR CLONING: A LABORATORY MANUAL, $2^{nd}$ edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

As used in the specification and claims, the singular form "a", "an" and "the" include plural references unless the context clearly dictates otherwise. For example, the term "a cell" includes a plurality of cells, including mixtures thereof.

Definitions:

The terms "polynucleotide", "nucleotide", "nucleic acid" and "oligonucleotide" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

A "nucleotide probe" or "probe" refers to a polynucleotide used for detecting or identifying its corresponding target polynucleotide in a hybridization reaction.

A "primer" is a short polynucleotide, generally with a free 3'-OH group, that binds to a target or "template" potentially present in a sample of interest by hybridizing with the target, and thereafter promoting polymerization of a polynucleotide complementary to the target.

"Operably linked" or "operatively linked" refers to a juxtaposition wherein the components so described are in a relationship permitting them to function in their intended manner. For instance, a promoter sequence is operably linked to a coding sequence if the promoter sequence promotes transcription of the coding sequence.

A "gene" refers to a polynucleotide containing at least one open reading frame that is capable of encoding a particular protein after being transcribed and translated.

The term "isolated", as used herein, means separated from constituents, cellular and otherwise, in which the polynucleotide, peptide, polypeptide, protein, antibody, or fragments thereof, are normally associated with in nature. As is apparent to those of skill in the art, a non-naturally occurring the polynucleotide, peptide, polypeptide, protein, antibody, or fragments thereof, does not require "isolation" to distinguish it from its naturally occurring counterpart. In addition, a "concentrated", "separated" or "diluted" polynucleotide, peptide, polypeptide, protein, antibody, or fragments thereof, is distinguishable from its naturally occurring counterpart in that the concentration or number of molecules per volume is greater than "concentrated" or less than "separated" than that of its naturally occurring counterpart. A polynucleotide, peptide, polypeptide, protein, antibody, or fragments thereof, which differs from the naturally occurring counterpart in its primary sequence or for example, by its glycosylation pattern, need not be present in its isolated form since it is distinguishable from its naturally occurring counterpart by its primary sequence, or alternatively, by another characteristic such as glycosylation pattern. Although not explicitly stated for each of the inventions disclosed herein, it is to be understood that all of the above embodiments for each of the compositions disclosed below and under the appropriate conditions, are provided by this invention. Thus, a non-naturally occurring polynucleotide is provided as a separate embodiment from the isolated naturally occurring polynucleotide. A protein produced in a bacterial cell is provided as a separate embodiment from the naturally occurring protein isolated from a eucaryotic cell in which it is produced in nature.

A "disease-associated" gene or polynucleotide refers to any gene or polynucleotide which is yielding transcription or translation products at an abnormal level or in an abnormal form in cells derived from a disease-affected tissues compared with tissues or cells of a non disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease. The transcribed or translated products may be known or unknown, and may be at a normal or abnormal level.

Different polynucleotides are said to "correspond" to each other if one is ultimately derived from another. For example, a sense strand corresponds to the anti-sense strand of the same double-stranded sequence. mRNA (also known as gene transcript) corresponds to the gene from which it is transcribed. cDNA corresponds to the RNA from which it has been produced, such as by a reverse transcription reaction, or by chemical synthesis of a DNA based upon knowledge of the RNA sequence. cDNA also corresponds to the gene that encodes the RNA. A polynucleotide may be said to correspond to a target polynucleotide even when it contains a contiguous portion of the sequence that share substantial sequence homology with the target sequence when optimally aligned.

As used herein, "expression" refers to the process by which a polynucleotide is transcribed into mRNA and/or the process by which the transcribed mRNA (also referred to as "transcript") is subsequently being translated into peptides, polypeptides, or proteins. The transcripts and the encoded polypeptides are collectedly referred to as "gene product". If the polynucleotide is derived from genomic DNA, expression may include splicing of the mRNA in an eukaryotic cell.

"Differentially expressed", as applied to nucleotide sequence or polypeptide sequence in a subject, refers to over-expression or under-expression of that sequence when compared to that detected in a control. Underexpression also encompasses absence of expression of a particular sequence as evidenced by the absence of detectable expression in a test subject when compared to a control.

"Differential expression" or "differential representation" refers to alterations in the abundance or the expression pattern of a gene product. An alteration in "expression pattern" may be indicated by a change in tissue distribution, or a change in hybridization pattern reviewed on a polynucleotide microarrays.

In the context of polynucleotides, a "linear sequence" or a "sequence" is an order of nucleotides in a polynucleotide in a 5' to 3' direction in which residues that neighbor each other in the sequence are contiguous in the primary structure of the polynucleotide. A "partial sequence" is a linear sequence of part of a polynucleotide which is known to comprise additional residues in one or both directions.

A linear sequence of nucleotides is "identical" to another linear sequence, if the order of nucleotides in each sequence is the same, and occurs without substitution, deletion, or material substitution. It is understood that purine and pyrimidine nitrogenous bases with similar structures can be functionally equivalent in terms of Watson-Crick base-pairing; and the inter-substitution of like nitrogenous bases, particularly uracil and thymine, or the modification of nitrogenous bases, such as by methylation, does not constitute a material substitution. An RNA and a DNA polynucleotide have identical sequences when the sequence for the RNA reflects the order of nitrogenous bases in the polyribonucleotides, the sequence for the DNA reflects the order of nitrogenous bases in the polydeoxyribonucleotides, and the two sequences satisfy the other requirements of this definition. Where one or both of the polynucleotides being compared is double-stranded, the sequences are identical if one strand of the first polynucleotide is identical with one strand of the second polynucleotide.

The term "hybridize" as applied to a polynucleotide refers to the ability of the polynucleotide to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. The hybridization reaction may constitute a step in a more extensive process, such as the initiation of a PCR reaction, or the enzymatic cleavage of a polynucleotide by a ribozyme.

When hybridization occurs in an antiparallel configuration between two single-stranded polynucleotides, the reaction is called "annealing" and those polynucleotides are described as "complementary". A double-stranded polynucleotide can be "complementary" or "homologous" to another polynucleotide, if hybridization can occur between one of the strands of the first polynucleotide and the second. "Complementarity" or "homology" (the degree that one polynucleotide is complementary with another) is quantifiable in terms of the proportion of bases in opposing strands that are expected to form hydrogen bonding with each other, according to generally accepted base-pairing rules.

Melting temperature of a primer refers to the temperature at which 50% of the prime-template duplexes are dissociated. Melting temperature is a function of ionic strength, base composition, and the length of the primer. It can be calculated using either of the following equations:

$$T_m(^\circ\text{ C.})=81.5+16.6\times\log[\text{Na}]+0.41\times(\%GC)-600/N$$

where [Na] is the concentration of sodium ions, and the % GC is in number percent, where N is chain length, or $$T_m(^\circ\text{ C.})=2\times(A+T)+4\times(C+G)$$

where A, T, G and C represent the number of adenosine, thymidine, guanosine and cytosine residues in the primer.

"In situ hybridization" is a well-established technique that allows specific polynucleotide sequences to be detected in morphologically preserved chromosomes, cells or tissue sections. In combination with immunocytochemistry, in situ hybridization can relate microscopic topological information to gene activity at the DNA, mRNA and protein level.

"Signal transduction" is a process during which stimulatory or inhibitory signals are transmitted into and within a cell to elicit an intracellular response. A "modulator of a signal transduction pathway" refers to a compound which modulates the activity of one or more cellular proteins mapped to the same specific signal transduction pathway. A modulator may augment or suppress the activity of a signaling molecule.

The terms "polypeptide", "peptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" refers to either natural and/or unnatural or synthetic amino acids, including glycine and both the D or L optical isomers, and amino acid analogs and peptidonimetics.

A "ligand" refers to a molecule capable of being bound by the ligand-binding domain of a receptor. The molecule may be chemically synthesized or may occur in nature. A ligand may be an "agonist" capable of stimulating the biological activity of a receptor, or an "antagonist" that inhibits the biological activity of a receptor.

"Cell surface receptors" or "surface antigens" are molecules anchored on the cell plasma membrane. They constitute a large family of proteins, glycoproteins, polysaccharides and lipids, which serve not only as structural constituents of the plasma membrane, but also as regulatory elements governing a variety of biological functions.

As used herein, "membrane proteins" include peripheral and integral membrane polypeptides that are bound to any cellular membranes including plasma membranes and membranes of intracellular organelles.

A "database" is a collection of data which has some common or distinct characteristics.

A "genetically engineered host cell" includes an individual cell or cell culture which can be or has been a recipient for vector(s) or for incorporation of nucleic acid molecules and/or proteins. Host cells include progeny of a single host cell, and the progeny may not necessarily be completely identical (in morphology or in genomic of total DNA complement) to the original parent cell due to natural, accidental, or deliberate mutation. A host cell includes cells transfected in vivo with a polynucleotide(s) of this invention.

"Luminescence" is the term commonly used to refer to the emission of light from a substance for any reason other than a rise in its temperature. In general, atoms or molecules emit photons of electromagnetic energy (e.g., light) when then move from an "excited state" to a lower energy state (usually the ground state); this process is often referred to as "radioactive decay". There are many causes of excitation. If exciting cause is a photon, the luminescence process is referred to as "photoluminescence". If the exciting cause is an electron, the luminescence process is referred to as "electroluminescence". More specifically, electroluminescence results from the direct injection and removal of electrons to form an electron-hole pair, and subsequent recombination of the electron-hole pair to emit a photon. Luminescence which results from a chemical reaction is usually referred to as "chemiluminescence". Luminescence produced by a living organism is usually referred to as "bioluminescence". If photoluminescence is the result of a spin-allowed transition (e.g., a single-singlet transition, triplet-triplet transition), the photoluminescence process is usually referred to as "fluorescence". Typically, fluorescence emissions do not persist after the exciting cause is removed as a result of short-lived excited states which may rapidly relax through such spin-allowed transitions. If photoluminescence is the result of a spin-forbidden transition (e.g., a triplet-singlet transition), the photoluminescence process is usually referred to as "phosphorescence". Typically, phosphorescence emissions persist long after the exciting cause is removed as a result of long-lived excited states which may relax only through such spin-forbidden transitions. A "luminescent label" may have any one of the above-described properties.

An "antigen" as used herein means a substance that is recognized and bound specifically by an antibody, a fragment thereof or by a T cell antigen receptor. Antigens can include peptides, proteins, glycoproteins, polysaccharides and lipids; portions thereof and combinations thereof. The antigens can be those found in nature or can be synthetic. They may be present on the surface or located within a cell.

As used in this invention, the term "epitope" is meant to include any determinant having specific affinity for the monoclonal antibodies of the invention. Epitopic determinants usually consist of chemically active surface groupings of molecules such as amino acids or sugar side chains and usually have specific three dimensional structural characteristics, as well as specific charge characteristics.

A "subject," "individual" or "patient" is used interchangeably herein, which refers to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

A "pharmaceutical composition" is intended to include the combination of an active agent with a carrier, inert or active, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin, REMINGTON'S PHARM. SCI., 15th Ed. (Mack Publ. Co., Easton (1975).

A "gene delivery vehicle" is defined as any molecule that can carry inserted polynucleotides into a host cell. Examples of gene delivery vehicles are liposomes, viruses, such as baculovirus, adenovirus and retrovirus, bacteriophage, cosmid, plasmid, fungal vectors and other recombination vehicles typically used in the art which have been described for expression in a variety of eukaryotic and prokaryotic hosts, and may be used for gene therapy as well as for simple protein expression.

A "viral vector" is defined as a recombinantly produced virus or viral particle that comprises a polynucleotide to be delivered into a host cell, either in vivo, ex vivo or in vitro. Examples of viral vectors include retroviral vectors, adenovirus vectors, adeno-associated virus vectors and the like. In aspects where gene transfer is mediated by a retroviral vector, a vector construct refers to the polynucleotide comprising the retroviral genome or part thereof, and a therapeutic gene. As used herein, "retroviral mediated gene transfer" or "retroviral transduction" carries the same meaning and refers to the process by which a gene or nucleic acid sequences are stably transferred into the host cell by virtue of the virus entering the cell and integrating its genome into the host cell genome. The virus can enter the host cell via its normal mechanism of infection or be modified such that it binds to a different host cell surface receptor or ligand to enter the cell. As used herein, retroviral vector refers to a viral particle capable of introducing exogenous nucleic acid into a cell through a viral or viral-like entry mechanism.

Retroviruses carry their genetic information in the form of RNA; however, once the virus infects a cell, the RNA is reverse-transcribed into the DNA form which integrates into the genomic DNA of the infected cell. The integrated DNA form is called a provirus.

In aspects where gene transfer is mediated by a DNA viral vector, such as an adenovirus (Ad) or adeno-associated virus (AAV), a vector construct refers to the polynucleotide comprising the viral genome or part thereof, and a therapeutic gene. Adenoviruses (Ads) are a relatively well characterized, homogenous group of viruses, including over 50 serotypes. (see, e.g., WO 95/27071) Ads are easy to grow and do not require integration into the host cell genome. Recombinant Ad-derived vectors, particularly those that reduce the potential for recombination and generation of wild-type virus, have also been constructed. (see, WO 95100655; WO 95/11984). Wild-type AAV has high infectivity and specificity integrating into the host cells genome. (Hermonat and Muzyczka (1984)*PNAS USA* 81:6466–6470; Lebkowski et al. (1988) *Mol. Cell Biol.* 8:3988–3996).

Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression.

Gene delivery vehicles also include several non-viral vectors, including DNA/liposome complexes, and targeted viral protein DNA complexes. Liposomes that also comprise a targeting antibody or fragment thereof can be used in the methods of this invention. To enhance delivery to a cell, the nucleic acid or proteins of this invention can be conjugated to antibodies or binding fragments thereof which bind cell surface antigens, e.g., TCR, CD3 or CD4.

Polynucleotides of the present invention

A central aspect of the present invention is the discovery of novel GPCR gene comprising a nucleic acid sequence depicted in any one of the FIGS. 1B, 1C, 1D, 2B, 3B, 4B, 5B, 6B, 7B, 8B, and 9B. In one aspect, the novel GPCR polynucleotides can be identified by first building Hidden Markov Models (hMMs) for sub-classes of GPCRs using SAM 3.0 (available from University of California, Santa Cruz), target-99 script as described in Hughey et al. (SAM: Sequence Alignment and Modeling Software System Technical Report UCSC-CRL-95-7, University of California, Santa Cruz, Computer Engineering). General methodology for building Hidden Markov Models are described in Haussler D et al. *J Mol Biol* (1994) February 4; Haussler D et al. 235(5):1501–31; *Ismb* (1993)1:47–55; and Baldi P et al. *J Comput Biol* (1994) Winter 1(4):311–36. The next step is to screen candidate gene sequences using SAM3.0 hmmscore algorithm, or the like, against the hMMs built for a specific class of GPCRs. An alignment using SAM 3.0 align2model was performed using the best hits against this hMMSs. In one aspect, the high-scoring protein sequences which match the hMM set are sorted so that the top 25, preferably top 10, more preferably top 5 entries have (a) no corresponding sequences in the non-redundant set (NCBI); and (b) no significant homology with hMMs for other families of proteins. Refinement of gene using GeneWise (Birney E et al. (2000) *Genome Res* (4):547-8) to map a known protein onto the portion of the genomic DNA. Each of the novel genes that match the family2B hMM best were searched against the Genbank non-redundant database (All non-redundant GenBank CDS translations+PDB+SwissProt+PIR+PRF) using BLASTed (Altschul) program to find close homologs. The nearest human homolog (or non-human) when there is no human entry) is then used as a probe for GeneWise to match against the portion of the contig from which the original gene was derived. For example, if A.ctgl5361-000002.13.0 is derived from contig 15361 of the human genome, a portion 50,000 base pairs longer in each direction from the predicted gene is extracted from the contig. Genewise then attempts to match the protein sequence against the genomic sequence best, defining the gene structure (introns and exons) based on the homolog and its knowledge of gene structure in general.

Like all other members of the GPCR superfamily, the invention GPCRs comprise a characteristic group of seven putative transmembrane spanning regions, an extracellular domain, and a cytoplasmic domain that interacts with specific downstream signal transduction components to transduce and amplify distinct arrays of intracellular signals.

In one embodiment, the present invention provides an isolated polynucleotide comprising a nucleic acid sequence encoding anyone of the seven transmembrane regions depicted in FIG. 10.

In a separate embodiment, the present invention provides an isolated polynucleotide comprising a nucleic acid sequence having at least about 90 nucleotides that is essentially identical to a linear sequence of comparable length contained in the sequence shown in any one of 1B, 1C, 1D, 2B, 3B, 4B, 5B, 6B, 7B, 8B, and 9B. Preferably, the isolated polynucleotide contains at least about 90 nucleotide bases, more preferably at least about 150 nucleotides, more preferably at least about 450 nucleotides, and even more preferably at least about 1200 nucleotides. In another embodiment, the isolated polynucleotide comprises a nucleic acid sequence of at least 90 nucleotides that encodes a polypeptide essentially identical to a linear sequence of at least 30 amino acids depicted in any one of the FIGS. 1A, 2A, 3A, 4A, 5A, 6A, 7A, 8A and 9A. Preferred linear peptide sequence is at least about 50 amino acids in length, more preferably at least 150 amino acids in length, and more preferably at least 400 amino acids. In yet another embodiment, the isolated polynucleotide is a complement of the above mentioned GPCR polynucleotides.

These gene sequences can be identified, in whole or in part, by specifically hybridizing under moderate or stringent conditions to the exemplary polynucleotides shown in any one of the FIGS. 1A, 2A, 3A, 4A, 5A, 6A, 7A, 8A and 9A. Alternatively, the invention sequences can be identified by their homology to published or known open reading frames, or pieces of genomic sequences using computer-assisted methods known in the art or those described herein.

Thus, in one aspect, a linear sequence of nucleotides is "essentially identical" to another linear sequence, if both sequences are capable of hybridizing to form a duplex with the same complementary polynucleotide. The term "hybridize" as applied to a polynucleotide refers to the ability of the polynucleotide to form a complex that is stabilized via hydrogen bonding between the bases of the nucleotide residues in a hybridization reaction. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. The hybridization reaction may constitute a step in a more extensive process, such as the initiation of a PCR reaction, or the enzymatic cleavage of a polynucleotide by a ribozyme.

Hybridization can be performed under conditions of different "stringency." Relevant conditions include temperature, ionic strength, time of incubation, the presence of additional solutes in the reaction mixture such as formamide, and the washing procedure. Higher stringency conditions are those conditions, such as higher temperature and lower sodium ion concentration, which require higher minimum complementarity between hybridizing elements for a stable hybridization complex to form. In general, a low stringency hybridization reaction is carried out at about 40° C. in about 10×SSC or a solution of equivalent ionic strength/temperature. A moderate stringency hybridization is typically performed at about 50° C. in about 6×SSC, and a high stringency hybridization reaction is generally performed at about 60° C. in about 1×SSC.

Sequences that hybridize under conditions of greater stringency are more preferred. As is apparent to one skilled in the art, hybridization reactions can accommodate insertions, deletions, and substitutions in the nucleotide sequence. Thus, linear sequences of nucleotides can be essentially identical even if some of the nucleotide residues do not precisely correspond or align. In general, essentially identical sequences of about 60 nucleotides in length will hybridize at about 50° C. in 10×SSC; preferably, they will hybridize at about 60° C. in 6×SSC; more preferably, they will hybridize at about 65° C. in 6×SSC; even more preferably, they will hybridize at about 70° C. in 6×SSC, or at about 40° C. in 0.5×SSC, or at about 30° C. in 6×SSC containing 50% formamide; still more preferably, they will hybridize at 40° C. or higher in 2×SSC or lower in the presence of 50% or more formamide. It is understood that the rigor of the test is partly a function of the length of the polynucleotide; hence shorter polynucleotides with the same homology should be tested under lower stringency and longer polynucleotides should be tested under higher stringency, adjusting the conditions accordingly. The relationship between hybridization stringency, degree of sequence-identity, and polynucleotide length is known in the art and can be calculated by standard formulae.

Sequence homology or identity can also be determined with the aid of computer methods. A variety of sequence analysis software programs are available in the art. Non-limiting examples of these programs are Bestfit program (Wisconsin Sequence Analysis Package, Genetics Computer Group, Madison Wis.), Fasta (Wisconsin Sequence Analysis Package, Genetics Computer Group, Madison Wis.), Blast (http://www.ncbi.nlm.nih.gov/BLAST/), DNA Star, MegAlign, GeneJocky, and SAM (Hughey et al. (1995) Technical Report UCSC-CRL-95-7, University of California, Santa Cruz, Computer Engineering). Sequence similarity is typically discerned by comparing a query sequence (polynucleotide or polypeptide sequence) to a reference sequence or a plurality of reference sequences contained in a database. Any public or proprietary sequence databases that contain DNA or protein sequences corresponding to a gene or a segment thereof can be used for sequence analysis. Commonly employed databases include but are not limited to GenBank, EMBL, DDBJ, PDB, SWISS-PROT, EST, STS, GSS, and HTGS. Common parameters for determining the extent of homology set forth by one or more of the aforementioned alignment programs include p value and percent sequence identity. P value is the probability that the alignment is produced by chance. For a single alignment, the p value can be calculated according to Karlin et al. (1990) *Prco.Natl. Acad. Sci* 87: 2264–2268. For multiple alignments, the p value can be calculated using a heuristic approach such as the one programmed in Blast. Percent sequence identity is defined by the ratio of the number of nucleotide or amino acid matches between the query sequence and the reference when the two are optimally aligned.

Polynucleotides that correspond or align more closely to the exemplary sequences disclosed herein are comparably more preferred. A query polynucleotide of at least 90 nucleotides is considered to be essentially identical to a reference polynucleotide (e.g. anyone of those sequences shown in of FIGS. 1B, 1C, 1D, 2B, 3B, 4B, 5B, 6B, 7B, 8B, and 9B.), when the query polynucleotide exhibits at least about 80% sequence identity, more preferably at least about 90% identity, even more preferably at least about 95% identity using any of the above-mentioned alignment programs with the default settings. Likewise, a query polypeptide is essentially identical to a reference polypeptide of at least 30 amino acids, when the query polypeptide shares at least 80% sequence identity, more preferably at least about 90% identity, even more preferably at least about 95% identity that can be discerned by the aforementioned programs using their respective default settings. When using Bestfit or any other sequence alignment program to determine whether a particular sequence is, for example, 80% identical to a reference sequence of the present invention, the percentage of identity is preferably calculated over a linear sequence of comparable length that is contained in the reference sequence. Typically, the upper limit of gaps in homology is set at 20% of the total number of amino acid residues or nucleotide residues in the respective reference sequence. The altered residues may occur at the amino or carboxyl terminal positions of the reference sequence or anywhere between those terminal positions, interspersed either individually among residues in the reference sequence or in one or more contiguous groups within the reference sequence. Allowable sequence alterations include but are not limited to deletion, insertion, translocation and substitution of individual residues.

Essentially identical sequences can also be characterized as possessing essentially the same functionality of the exemplary nucleic acids. Functionality may be established by different criteria, which includes the ability to, (a) hybridize with a target polynucleotide; (b) effectively amplify a target sequence to yield a substantially homogenous multiplicity of products; (c) extend the 3' end sequence complementary to a target sequence in a nucleotide sequencing reaction; and (d) function in substantially the same manner to produce essentially the same protein product as the nucleic acid exemplified herein, by virtue of the degeneracy of the genetic codes, or that have conservative amino acid substitutions. Suitable amino acid substitutions may be made on the basis of similarity in polarity, charge, solubility, hydrophobicity, hydrophilicity, and/or the amphipathic nature of the residues as long as the functional characteristics of the GPCR polynucleotide is retained. For instance, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine and; phenylalanine and tyrosine The polynucleotides of the present invention can also comprise heterologous sequences that it is not naturally found linked to the sequences shown in any one of FIGS. 1B, 1C, 1D, 2B, 3B, 4B, 5B, 6B, 7B, 8B, and 9B. The choice of heterologous sequences is largely dependent on the intended purpose. Where desired, the heterologous sequence may encode a polypeptide that facilitates detection of the expression and purification of the gene product. Examples of such sequences are known in the art and include those encoding reporter proteins such as β-galactosidase, β-lactamase, chloramphenicol acetyltransferase (CAT), luciferase, green fluorescent protein (GFP) and their derivatives. Other heterologous sequences that facilitate purification include epitopes such as Myc, HA (derived from influenza virus hemagglutinin), His-6, FLAG, glutathione S-transferase (GST), maltose-binding protein (MBP), or the Fc portion of immunoglobulin. The heterologous sequences may also code for polypeptides that direct the intracellular localization of the expressed gene product. Examples of this class of heterologous sequences include but are not limited to those codes for a leader sequence that effects secretion of the gene product; membrane localization signal sequence that anchors a protein to the intracellular membranous structures, such as plasma membrane, nucleus, Golgi apparatus, endoplasmic reticulum, endosome, lysosome, and mitochondria. One skilled in the art can readily fashion a vast diversity of heterologous sequences based on the wealth of genetic data available in the art.

The polynucleotides embodied in the invention also include nucleotide sequences that encode full-length GPCR, mutant GPCR, peptide fragments of the full-length GPCR, truncated GPCR, and GPCR fusion proteins. These include, but are not limited to nucleotide sequences encoding mutant GPCR isolated by the methods disclosed herein; polypeptides or peptides corresponding to one or more of the extracellular domains, or transmembrane and/or cytoplasmic domains of the GPCR or portions of these domains; truncated GPCR in which one or two of the domains is deleted, e.g., a soluble GPCR lacking a transmembrane domain, or both a transmembrane and cytosolic regions, or a truncated, nonfunctional GPCR lacking all, or a portion of a cytosolic region. Nucleotides encoding fusion proteins may include by are not limited to full length GPCR, truncated GPCR or peptide fragments of GPCR fused to an unrelated protein or peptide, such as for example, a transmembrane sequence, which anchors the GPCR extracellular domains to the cell membrane; an Ig Fc domain which increases the stability and half life of the resulting fusion protein (e.g., GPCR-Ig) in the bloodstream; or an enzyme, fluorescent protein, luminescent protein which can be used as a marker.

Larger gene fragments containing or corresponding to the GPCR polynucleotides of the invention can readily be isolated, without undue experimentation using a variety of recombinant DNA techniques. These large fragments can be full-length GPCR cDNAs, mutant GPCR polynucleotides, splice variants of the exemplary GPCR, or GPCR homologs expressed in other species. The identification of homologs of GPCR in related species can be useful for developing animal model systems more closely related to humans for purposes of drug discovery. For example, expression libraries of cDNAs synthesized from MnRNA derived from the organism of interest can be screened using labeled natural GPCR ligand derived from that species, e.g., a synthetic or natural GPCR ligand fusion protein. Alternatively, such cDNA libraries, or genomic DNA libraries derived from the organism of interest can be screened by hybridization using the polynucleotides described herein as hybridization or amplification probes. Furthermore, genes at other genetic loci within the genome that encode proteins which have extensive homology to one or more domains of the GPCR gene product can also be identified via similar techniques. For cDNA libraries, such screening techniques can identify clones derived from alternatively spliced transcripts in the same or different species.

Expression libraries may also be employed to screen for homologs, mutants or splice variants. An expression library can typically be constructed utilizing cDNA synthesized from, for example, RNA isolated from a tissue known, or suspected, to express a mutant GPCR allele in an individual suspected of or known to carry such a mutant allele. In this manner, gene products made by the putatively mutant tissue may be expressed and screened using standard antibody screening techniques in conjunction with antibodies raised against the normal GPCR gene product, as described, below. For screening techniques, see, for example, Harlow, E. and Lane, eds., 1988, "Antibodies: A Laboratory Manual", Cold Spring Harbor Press, Cold Spring Harbor. Additionally, screening can be accomplished by screening with labeled natural or synthetic GPCR ligand or ligand fusion proteins. In cases where an GPCR mutation results in an expressed gene product with altered function (e.g., as a result of a missense or a frameshift mutation), a polyclonal set of antibodies to GPCR are likely to cross-react with the mutant GPCR gene product. Library clones detected via their reaction with such labeled antibodies can be purified and subjected to sequence analysis according to methods well known to those of skill in the art.

The cDNA or genomic library screens can be carried out on arrays immobilized with candidate sequences. Suitable arrays include conventional filters, DNA microarrays such as DNA chips manufactured by Affymetrix or Incyte Genomics. The labeled probe may contain at least about 15–30 base pairs of the GPCR nucleotide sequence, as shown in any one of FIGS. 1B, 1C, 1D, 2B, 3B, 4B, 5B, 6B, 7B, 8B , and 9B. The hybridization washing conditions used should be of a lower stringency when the cDNA library is derived from an organism different from the type of organism from which the labeled sequence was derived.

Low stringency conditions are well known to those of skill in the art, and will vary predictably depending on the specific organisms from which the library and the labeled sequences are derived. For guidance regarding such conditions see, for example, Sambrook et al., 1989, Molecular Cloning, A Laboratory Manual, Cold Springs Harbor Press, N.Y.; and Ausubel et al., 1989, Current Protocols in Molecular Biology, Green Publishing Associates and Wiley Interscience, N.Y.

Alternatively, the labeled GPCR nucleotide probe may be used to screen a genomic library derived from the organism of interest, using appropriately stringent conditions. The identification and characterization of human genomic clones is helpful for designing diagnostic tests and clinical protocols for treating disorders in human patients. For example, sequences derived from regions adjacent to the intron/exon boundaries of the human gene can be used to design primers for use in amplification assays to detect mutations within the exons or introns that can be used in diagnostics.

Furthermore, an GPCR gene homolog may be isolated from nucleic acid of the organism of interest by performing amplification procedures using two degenerate oligonucleotide primer pools designed on the basis of amino acid sequences within the GPCR gene product disclosed herein. For the purpose of this invention, amplification means any method employing a primer-dependent polymerase capable of replicating a target sequence with reasonable fidelity. Amplification may be carried out by natural or recombinant DNA-polymerases such as T7 DNA polymerase, Klenow fragment of *E. coli* DNA polymerase, Taq polymerase, pfu polymerase and/or RNA polymerases such as reverse transcriptase. A preferred amplification method is PCR. General procedures for PCR are taught in U.S. Pat. No. 4,683195 (Mullis et al.) and U.S. Pat. No. 4,683,202 (Mullis et al.). However, optimal PCR conditions used for each application reaction are generally empirically determined or estimated with a computer software commonly employed by artisans in the field. A number of parameters influence the success of a reaction. Among them are annealing temperature and time, extension time, $Mg^{2+}$ ATP concentration, pH, and the relative concentration of primers, templates, and deoxyribonucleotides.

The template for the reaction may be cDNA obtained by reverse transcription of mRNA prepared from cell lines or tissue known or suspected to express a GPCR gene allele. The PCR product may be subcloned and sequenced to ensure that the amplified sequences represent the sequences of a GPCR gene. The PCR fragment may then be used to isolate a full length cDNA clone by a variety of methods. For example, the amplified fragment may be labeled and used to screen a cDNA library, such as a bacteriophage cDNA library. Alternatively, the labeled fragment may be used to isolate genomic clones via the screening of a genomic library.

Amplification procedures can also be utilized to isolate full-length cDNA sequences. A representative amplification technique applicable for gene cloning is 5'-RACE-PCR. In this technique, the poly-A mRNA that contains the coding sequence of particular interest is first identified by hybridization to a sequence disclosed herein and then reverse transcribed with a 3'-primer comprising the sequence disclosed herein The newly synthesized cDNA strand is then tagged with an anchor primer of a known sequence, which preferably contains a convenient cloning restriction site attached at the 5'end. The tagged cDNA is then amplified with the 3'-primer (or a nested primer sharing sequence homology to the internal sequences of the coding region) and the 5'-anchor primer. The amplification may be conducted under conditions of various levels of stringency to optimize the amplification specificity. 5'-RACE-PCR can be readily performed using commercial kits (available from, e.g., BRL Life Technologies Inc, Clotech) according to the manufacturer's instructions.

The exemplary GPCR gene sequences can also be employed to isolate mutant GPCR gene alleles. Such mutant alleles may be isolated from individuals either known or proposed to have a genotype which contributes to the symptoms of disorders arising from the aberrant expression or activity of the GPCR protein. By comparing the DNA sequence of the mutant GPCR allele to that of the normal GPCR allele, the mutation(s) responsible for the loss or alteration of function of the mutant GPCR gene product can be ascertained. Mutant alleles and mutant allele products may then be utilized in the therapeutic and diagnostic systems described herein. Additionally, such GPCR gene sequences can be used to detect GPCR gene regulatory (e.g., promoter or promoter/enhancer) defects which can affect the expression of the GPCRP.

The polynucleotides embodied in this invention can be conjugated with a detectable label. Such polynucleotides are useful, for example, as probes for detection of related nucleotide sequences. Detectable labels suitable for use in the present invention include any composition detectable by spectroscopic, photochemical, biochemical, immunochemical, electrical, optical or chemical means. A wide variety of appropriate detectable labels are known in the art, which include luminescent labels, radioactive isotope labels, enzymatic or other ligands. In preferred embodiments, one will likely desire to employ a fluorescent label or an enzyme tag, such as digoxigenin, β-galactosidase, urease, alkaline phosphatase or peroxidase, avidin/biotin complex. The labels may be incorporated by any of a number of means well known to those of skill in the art. In one aspect, the label is simultaneously incorporated during the amplification step in the preparation of the invention polynucleotides. Thus, for example, polymerase chain reaction (PCR) with labeled primers or labeled nucleotides can provide a labeled amplification product. In a separate aspect, transcription reaction, as described above, using a labeled nucleotide (e.g. fluorescein-labeled UTP and/or CTP, digoxigenin-UTP) or a labeled primer, incorporates a detectable label into the transcribed nucleic acids.

Alternatively, a label may be added directly to the original polynucleotide sample (e.g., mRNA, polyA, MRNA, cDNA, etc.) or to the amplification product after the amplification is completed. Means of attaching labels to nucleic acids are well known to those of skill in the art and include, for example nick translation or end-labeling (e.g. with a labeled RNA) by kinasing of the polynucleotides and subsequent attachment (ligation) of a nucleic acid linker to a label (e.g., a fluorophore).

The polynucleotides of this invention can be obtained by chemical synthesis, recombinant cloning, e.g. PCR, or any combination thereof. Methods of chemical polynucleotide synthesis are well known in the art and need not be described in detail herein. One of skill in the art can use the sequence data provided herein to obtain a desired polynucleotide by employing a DNA synthesizer, PCR machine, or ordering from a commercial service.

Uses of the polynucleotides of the present invention

The polynucleotides of this invention have several uses. GPCR polynucleotides are useful, for example, in expression systems for the production of GPCR or GPCR fragments. They are also useful as hybridization probes to clone the full-length GPCR cDNA as described above, or to assay for the presence of GPCR sequences in a sample using methods well known to those in the art. The hybridization assays employing such probes have numerous applications including but not limited to GPCR gene expression analysis, fingerprinting, sequence mapping, GPCR chromosomal localization and polymorphism detection. Furthermore, the polynucleotides are useful as primers to effect amplification of desired polynucleotides. The polynucleotides of this invention are also useful in antibody production, disease diagnosis, prognosis, and treatment.

Methods for conducting the aforementioned genetic analysis using the polynucleotides of the present invention are well known to artisans in the field (see Sambrook, supra), and hence are not detailed herein. Briefly, representative techniques include Southern hybridization, gene chip assays (e.g. U.S. Pat. No. 5,445,934 Fodor et al.), amplification procedures (e.g. PCR, RT-PCR), FISH, SAGE (Velculescu, et al. (1995) *Science* 270:484–487 and U.S. Pat. No. 5,695,937 Kinzler et al.), in-situ hybridization, nucleotide sequencing, restriction fragment length polymorphism (RFLP), single-strand conformation polymorphism assay, and allele-specific oligonucleotide hybridization.

Vectors, host cells, and transgenic organisms of the present invention

The polynucleotides of the present invention can be inserted into a suitable gene delivery vehicle, and the vehicle in turn can be introduced into a suitable host cell for replication and amplification. Accordingly, this invention further provides a variety of gene delivery vehicles comprising the polynucleotide of the present invention. Gene delivery vehicles include both viral and non-viral vectors. Non-limiting examples of gene delivery vehicles are liposomes, plasmid, bacteriophage, cosmid, fungal vectors, viruses, such as adenovirus, baculovirus, and retrovirus, and any other recombination vehicles capable of carrying an inserted polynucleotide into a host cell.

Vectors are generally categorized into cloning and expression vectors. Cloning vectors are useful for obtaining replicate copies of the polynucleotides they contain, or as a means of storing the polynucleotides in a depository for future recovery. Expression vectors (and host cells containing these expression vectors) can be used to obtain polypeptides produced from the polynucleotides they contain. Suitable cloning and expression vectors include any known in the art, e.g., those for use in bacterial, mammalian, yeast and insect expression systems. The polypeptides produced in the various expression systems are also within the scope of the invention.

Cloning and expression vectors typically contain a selectable marker (for example, a gene encoding a protein necessary for the survival or growth of a host cell transformed with the vector), although such a marker gene can be carried on another polynucleotide sequence co-introduced into the host cell. Only those host cells into which a selectable gene has been introduced will grow under selective conditions. Typical selection genes either: (a) confer resistance to antibiotics or other toxins, e.g., ampicillin, neomycin, methotrexate; (b) complement auxotrophic deficiencies; or (c) supply critical nutrients not available from complex media. The choice of the proper marker gene will depend on the host cell, and appropriate genes for different hosts are known in the art. Vectors also typically contain a replication system recognized by the host.

Suitable cloning vectors can be constructed according to standard techniques, or selected from a large number of cloning vectors available in the art. While the cloning vector selected may vary according to the host cell intended to be used, useful cloning vectors will generally have the ability to self-replicate, may possess a single target for a particular restriction endonuclease, or may carry marker genes. Suitable examples include plasmids and bacterial viruses, e.g., pBR322, pMB9, ColE1, pCR1, RP4, pUC18, mp18, mp19, phage DNAs, and shuttle vectors such as pSA3 and pAT28. These and other cloning vectors are available from commercial vendors such as Stratagene, Clontech, BioRad, and Invitrogen.

Expression vectors containing the GPCR polynucleotides are useful to obtain host vector systems to produce GPCR polypeptides. It is implied that these expression vectors must be replicable in the host organisms either as episomes or as an integral part of the chromosomal DNA. Typically, the GPCR polynucleotide of interest is operably linked to a regulatory element that directs the expression of the GPCR polypeptide. As used herein, regulatory elements include but are not limited to inducible and non-inducible promoters, enhancers, operators and other elements known to those skilled in the art that drive and regulate expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors.

A variety of host-expression vector systems may be utilized to express a GPCR polynucleotide of the invention. Where the GPCR peptide or polypeptide is a soluble derivative (e.g., a GPCR peptide corresponding to the extracellular domain; truncated or deleted GPCR in which the transmembrane and/or cytosolic domain are deleted) the peptide or polypeptide can be recovered from the culture, i.e., from the host cell in cases where the GPCR peptide or polypeptide is not secreted, and from the culture media in cases where the GPCR peptide or polypeptide is secreted by the cells. However, the expression systems also encompass engineered host cells that express the GPCR or functional equivalents in situ, i.e., anchored in the cell membrane. Purification or enrichment of the GPCR from such expression systems can be accomplished using appropriate detergents and lipid micelles and methods well known to those skilled in the art. However, such engineered host cells themselves may be used in situations where it is important not only to retain the structural and functional characteristics of the GPCR, but to assess biological activity, e.g., in drug screening assays.

The expression systems that may be used for purposes of the invention include but are not limited to microorganisms such as bacteria (e.g., *E. coli, B. subtilis*) transformed with recombinant bacteriophage DNA, plasmid DNA or cosmid DNA expression vectors containing GPCR polynucleotides; yeast (e.g., Saccharomyces, Pichia) transformed with recombinant yeast expression vectors containing the GPCR polynucleotides; insect cell systems infected with recombinant virus expression vectors (e.g., baculovirus) containing the GPCR sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing GPCR polynucleotides; or mammalian cell systems (e.g., COS, CHO, BIK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the GPCR gene product being expressed. For example, when a large quantity of such a protein is to be produced, for the generation of pharmaceutical compositions of GPCR protein or for raising antibodies to the GPCR protein, for example, vectors which direct the expression of high levels of fusion protein products that are readily purified may be desirable. Such vectors include, but are not limited, to the *E. coli* expression vector pUR278 (Ruther et al., 1983, EMBO J. 2:1791–1794), in which the GPCR coding sequence maybe ligated individually into the vector in frame with the lacZ coding region so that a fusion protein is produced; pIN vectors (Inouye & Inouye, 1985, Nucleic Acids Res. 13:3101–3110; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In an insect system, Autographa californica nuclear polyhidrosis virus (AcNPV) is used as a vector to express foreign genes. The virus grows in *Spodoptera frugiperda* cells. The GPCR gene coding sequence may be cloned individually into non-essential regions (for example the polyhedrin gene) of the virus and placed under control of an AcNPV promoter (for example the polyhedrin promoter). Successful insertion of GPCR gene coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (E.g, see, Schroeder et al., U.S. Pat. No. 4,215,051).

In mammalian host cells, a number of viral-based expression systems may be utilized. In cases where an adenovirus is used as an expression vector, the GPCR nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the GPCR gene product in infected hosts. (E.g., See Logan & Shenk, 1984, Proc. Natl. Acad. Sci. USA 81:3655–3659). Specific initiation signals may also be required for efficient translation of inserted GPCR nucleotide sequences. These signals include the ATG initiation codon and adjacent sequences. In cases where an entire GPCR gene or cDNA, including its own initiation codon and adjacent sequences, is inserted into the appropriate expression vector, no additional translational control signals may be needed. However, in cases where only a portion of the GPCR coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bitter et al., 1987, Methods in Enzymol. 153:516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. For instance, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3 and WI38.

For long-term, high-yield production of recombinant proteins, stable expression is preferred. For example, cell lines which stably express the GPCR sequences described above may be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the GPCR gene product Such engineered cell lines may be particularly useful in screening and evaluation of compounds that affect the endogenous activity of the GPCR gene product.

A number of selection systems may be used, including but not limited to the herpes simplex virus thymidine kinase (Wigler, et al., 1977, Cell 11:223–232), hypoxanthine-guanine phosphoribosyltransferase, and adenine phosphoribosyltransferase (Lowy, et al., 1980, Cell 22:817–823) genes can be employed in $tk^-$, $hgprt^-$ or $aprt^-$cells, respectively. Also, antimetabolite resistance can be used as the basis of selection for the following genes: dhfr, which confers resistance to methotrexate (Wigler, et al., 1980, Natl. Acad. Sci. USA 77:3567–3570; O'Hare, et al., 1981, Proc. Natl. Acad. Sci. USA 78:1527–1531); gpt, which confers resistance to mycophenolic acid (Mulligan & Berg, 1981, Proc. Natl. Acad. Sci. USA 78:2072–2076); neo, which confers resistance to the aminoglycoside G-418 (Colbere-Garapin, et al., 1981, J. Mol. Biol. 150:1–14); and hygro, which confers resistance to hygromycin (Santerre, et al., 1984, Gene 30:147–156).

Alternatively, any fusion protein may be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88: 8972–8976). In this system, the gene of interest is subcloned into a vaccinia recombination plasmid such that the gene's open reading fame is translationally fused to an amino-terminal tag consisting of six histidine residues. Extracts from cells infected with recombinant vaccinia virus are loaded onto $Ni^{2+}$. nitriloacetic acid-agarose columns and histidine-tagged proteins are selectively eluted with imidazole-containing buffers.

The GPCR gene products can also be expressed in transgenic animals. Animals of any species, including, but not limited to, mice, rats, rabbits, guinea pigs, pigs, micro-pigs, goats, and non-human primates, e.g., baboons, monkeys, and chimpanzees may be used to generate GPCR transgenic animals.

Any technique known in the art may be used to introduce the GPCR transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (van derPutten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the GPCR transgene in all their cells, as well as animals which carry the transgene in some, but not all their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al. (Lasko, M. et al., 1992, Proc. Natl. Acad. Sci. USA 89: 6232–6236). The regulatory sequences required for such a cell-type specific activation will depend upon the particular cell type of interest, and will be apparent to those of skill in the art. When it is desired that the GPCR gene transgene be integrated into the chromosomal site of the endogenous GPCR gene, gene targeting is preferred. Briefly, when such a technique is to be utilized, vectors containing some nucleotide sequences homologous to the endogenous GPCR gene are designed for the purpose of integrating, via homologous recombination with chromosomal sequences, into and disrupting the function of the nucleotide sequence of the endogenous GPCR gene. The transgene may also be selectively introduced into a particular cell type, thus inactivating the endogenous GPCR gene in only that cell type, by following, for example, the teaching of Gu et al. (Gu, et al., 1994, Science 265: 103–106). The regulatory sequences required for such a cell-type specific inactivation will depend upon the particular cell type of interest, and will be apparent to those of skill in the art.

Once transgenic organisms have been generated, the expression of the recombinant GPCR gene may be assayed utilizing standard techniques. Initial screening may be accomplished by Southern blot analysis or PCR techniques to analyze tissues of the transgenic organism to assay whether integration of the transgene has taken place. The level of mRNA expression of the transgene in the tissues of the transgenic organism may also be assessed using techniques which include but are not limited to Northern blot analysis of tissue samples obtained from the organism, in situ hybridization analysis, and RT-PCR. Samples of GPCR gene-expressing tissue, may also be evaluated immunocytochemically using antibodies specific for the GPCR transgene product Polypeptides and antibodies of the present invention This invention encompasses proteins or polypeptides expressed from the polynucleotides of this invention, which are intended to include wild-type, chemically synthesized and recombinantly produced polypeptides and proteins from prokaryotic and eukaryotic host cells, as well as muteins, analogs and fragments thereof. In some embodiments, the term also includes various types of antibodies that specifically bind to the GPCR polypeptides.

Also encompassed by this embodiment are proteins functionally equivalent to the GPCR encoded by the polynucleotides described in the aforementioned section. A "functional equivalent" varies from the wild-type sequence by any combination of addition, deletion, or substitution while preserving at least one functional property of the invention GPCR relevant to the context in which it is being tested. Relevant GPCR functional properties include but are not limited to the ability of the equivalent polypeptide to bind natural GPCR ligand, the ability to interact with downstream molecules such as heterotrimeric G proteins, the ability to elicit GPCR cellular responses including, e.g. ion flux, mobilization of $Ca^{2+}$ from intracellular stores, tyrosine or serine phosphorylation, or change in cellular phenotype when the GPCR equivalent is present in an appropriate cell type. Such functionally equivalent GPCR proteins may contain amino acid substitutions introduced on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, teonine, cysteine, tyrosine, asparagine, and glutamine; positively charged (basic) amino acids include arginine, lysine, and histidine; and negatively charged (acidic) amino acids include aspartic acid and glutamic acid.

Whereas random mutations can be introduced to GPCR polynucleotides (using methods well established in the art), and the resulting mutant GPCRs tested for GPCR activity, site-directed mutation is preferred to generate mutant GPCRs with an altered GPCR functional property or expression profile. These alterations in GPCR function may evince an increase in binding affinity for natural GPCR ligand, and/or greater signaling capacity; or a decrease in ligand binding affinity and/or signal transduction capacity; or differential expression of GPCR in various body tissues or intracellular compartments.

In designing mutant GPCRs, it is preferably to discern the boundaries of various domains that are conserved amongst homologs from selected species. For example, regions of identity may be determined by alignment of GPCR (FIGS. 6–8) with GPCR homologs from other species. Mutant GPCRs can be engineered so that regions of identity are maintained, whereas the variable residues are altered, e.g., by addition, deletion or insertion of one or more conservative amino acid residue(s). Where alteration of function is desired, deletion or non-conservative alterations of the conserved regions can be engineered. For example, deletion or non-conservative alterations (substitutions or insertions) of the cytoplasmic domain can be introduced so as to alter the signaling path of the resulting GPCR. Specifically, the cytoplasmic domain of a Gi- or Gs-coupled GPCR may be mutated to mimic that of Gq-coupled receptor, so as to effect q-type downstream signaling, such as calcium mobilization, that is readily amenable to high throughput screening techniques.

Other mutations to the GPCR coding sequence can be made to generate GPCRs that are better suited for expression, scale up, etc. in the host cells chosen. For example, cysteine residues can be deleted or substituted with another amino acid in order to eliminate non-essential disulfide bridges; Non-essential N-linked glycosylation sites can be altered or eliminated to achieve, for example, expression of a homogeneous product that is more easily recovered and purified from yeast hosts which are known to hyperglycosylate N-linked sites. For instance, a variety of amino acid substitutions at one or both of the first or third amino acid positions of any one or more of the glycosylation recognition sequences which occur in the ECD (N-X-S or N-X-T), and/or an amino acid deletion at the second position of any one or more such recognition sequences in the extracellular domain will prevent glycosylation of the GPCR at the modified tripeptide sequence (see, e.g., Miyajima et al., 1986, EMBO J. 5(6):1193–1197).

As noted above, GPCR has a characteristic group of seven putative transmembrane spanning regions, which form a serpentine structure with hydrophilic domains located between the transmembrane domains, arranged alternately outside and within the cell to form the extracellular and cytoplasmic domains of the receptor. Polypeptides corresponding to one or more domains of the GPCR (e.g., extracelllar, transmembrane or cytoplasmic domain), truncated or deleted GPCRs (e.g., GPCR in which the transmembrane and/or cytoplasmic domain is deleted) as well as fusion proteins in which the full length GPCR, a GPCR peptide or truncated GPCR is fused to an unrelated protein, or one or more domains of a GPCR of a different class, are also within the scope of the invention. Useful fusion partners include sequences that facilitate the intracellular localization of the altered GPCR, or enhance immunological reactivity or the coupling of the polypeptide to an immunoassay support of a vaccine carrier. As such, the resulting fusion proteins include but are not limited to (a) immunoglobulin fusions which stabilize the GPCR protein or peptide and prolong half-life in vivo; (b) fiusions to unrelated proteins or epitopes (e.g. GST, flu-tagg, myc-tag, FLAG-tag) to facilitate protein purification; (c) fusions to a signal sequence that directs the fusion protein to the cell membrane, or that allows the extracellular domain to be displayed on the cell surface; (d) fusions to the extracellular domain of a different class of GPCR, so as to alter the binding specificity of the fusion GPCR; (e) fusions to the cytoplasmic domain of a different class of GPCR to effect shunting of downstream signaling to a different pathway, which may be more amenable to a high throughput analysis.

The polypeptides of the invention can also be conjugated to a chemically functional moiety. Typically, the moiety is a label capable of producing a detectable signal. These conjugated polypeptides are useful, for example, in detection systems for diagnosis and screening assays described herein. A wide variety of labels are known in the art. Non-limiting examples of the types of labels which can be used in the present invention include radioisotopes, enzymes, colloidal metals, and luminescent compounds.

The polypeptides of this invention also can be combined with various liquid phase carriers, such as sterile or aqueous solutions, pharmaceutically acceptable carriers, suspensions and emulsions. Examples of non-aqueous solvents include propyl ethylene glycol, polyethylene glycol and vegetable oils. When used to prepare antibodies, the carriers also can include an adjuvant that is useful to non-specifically augment a specific immune response. A skilled artisan can easily determine whether an adjuvant is required and select one. However, for the purpose of illustration only, suitable adjuvants include, but are not limited to Freund's Complete and Incomplete, mineral salts and polynucleotides.

The polypeptides of this invention can be prepared by a number of processes well known to those of skill in the art. Representative techniques are purification, chemical synthesis and recombinant methods. Cellular GPCR can be purified from tissues or cells expressing the GPCR by methods such as immunoprecipitation with antibody, and standard techniques such as gel filtration, ion-exchange, reversed-phase, and affinity chromatography using a fusion protein as shown herein. For such methodology, see for example Deutscher et al. (1999) GUIDE TO PROTEIN PURIFICATION: METHODS IN ENZYMOLOGY (Vol. 182, Academic Press).

Alternatively, the polypeptides also can be obtained by chemical synthesis using a commercially available automated peptide synthesizer such as those manufactured by Perkin Elmer/Applied Biosystems, Inc., Model 430A or 431A, Foster City, Calif., USA. The synthesized protein or polypeptide can be precipitated and further purified, for example by high performance liquid chromatography (HPLC). In addition, the invention polypeptides can be generated recombinantly by expressing polynucleotides using the vector systems and host cells as described in the section above.

This invention further provides antibodies that specifically bind to one or more epitopes of GPCR, or epitopes of conserved variants of GPCR, or peptide fragments of the GPCR. Such antibodies include but are not limited to polyclonal antibodies, monoclonal antibodies (mAbs), Fab, Fab', $F(ab')_2$ fragments, humanized or chimeric antibodies, single chain antibodies, anti-idiotypic (anti-Id) antibodies, and epitope-binding fragments of any of the above.

The production of these antibodies and epitope-binding fragments are well established in the art. For instance, Fab fragments may be generated by digesting a whole antibody with papain and contacting the digest with a reducing agent to reductively cleave disulfide bonds. Fab' fragments may be obtained by digesting the antibody with pepsin and reductive cleavage of the fragment so produce with a reducing agent. In the absence of reductive cleavage, enzymatic digestion of the monoclonal with pepsin produces $F(ab')_2$ fragments. Alternatively, Fab fragments can be recombinantly produced by a Fab expression library (see, e.g. Huse et al., 1989, Science, 246:1275–1281).

For production of polyclonal antibodies, an appropriate host animal is immunized with substantially purified GPCR polypeptide, whether the full-length GPCR, mutant GPCR, functional equivalents, fusion GPCR, or a fragment of any of the above. Suitable host animals may include but are not limited to mouse, rabbits, mice, and rats. The GPCR polypeptide is introduced commonly by injection into the host footpads, via intramuscular, intraperitoneal, or intradermal routes. Peptide fragments suitable for raising antibodies may be prepared by chemical synthesis, and are commonly coupled to a carrier molecule (e.g., keyhole limpet hemocyanin), or admixed with adjuvants to enhance the immunogenicity of the antigen. Depending on the host species, suitable adjuvants can be Freund's (complete and incomplete), mineral gels such as aluminum hydroxide, surface active substances such as lysolecithin, pluronic polyols, polyanions, peptides, oil emulsions, dinitrophenol, and potentially useful human adjuvants such as BCG (bacille Calmette-Guerin) and *Corynebacterium parvum.*

Sera harvested from the immunized animals provide a source of polyclonal antibodies. Detailed procedures for purifying specific antibody activity from a source material are known within the art. Undesired activity cross-reacting with other antigens, if present, can be removed, for example, by running the preparation over adsorbants made of those antigens attached to a solid phase and eluting or releasing the desired antibodies off the antigens. If desired, the specific antibody activity can be further purified by such techniques as protein A chromatography, ammonium sulfate precipitation, ion exchange chromatography, high-performance liquid chromatography and immunoannnity chromatography on a column of the immunizing polypeptide coupled to a solid support The generation of monoclonal antibodies, which are homogeneous populations of antibodies to a particular antigen, can be carried out by any technique which provides for the production of antibody molecules by continuous cell lines in culture. These include, but are not limited to, the hybridoma technique of Kohler and Milstein (1975) Nature 256:495–497 and U.S. Pat. No. 4,376,110, the human B-cell hybridoma technique, and the EBV-hybridoma technique (Cole et al., 1985, Monoclonal Antibodies And Cancer Therapy, Alan R. Liss, Inc., pp. 77–96).

Monoclonal antibodies to the GPCR can, in turn, be utilized to generate anti-idiotype antibodies (Greenspan & Bona, 1993, FASEB J 7(5):437–444; and Nisonoff, 1991, J. Immunol. 147(8):2429–2438), which recognize unique epitopes present on the monoclonal antibody. Of particular interest is the type of anti-idiotype antibodies that "mimic" the GPCR epitope which is recognized by the parent monoclonal antibody. For instance, the parent monoclonal antibody capable of binding to the GPCR extracellular domain, and competitively inhibiting the binding of natural GPCR ligand to the GPCR can be used to generate anti-idiotypes that "mimic" the extracellular domain and, therefore, bind and neutralize natural GPCR ligand. Such neutralizing anti-idiotypes or Fab fragments of such anti-idiotypes are particularly useful in therapeutic regimens to neutralize the physiological activity of the natural GPCR ligand.

Also encompassed in this embodiment are "chimeric antibodies" in which various portions are derived from different animal species. A "humanized antibody" is a type of chimeric antibody in which all regions except the antigen binding portions (also referred to as "CDRs") are derived from a non-human species. Such antibody can be produced by fusing the constant regions of the heavy and light chains of a human immunoglobulin with the variable regions of a murine antibody that confirm the antigen-binding specificity. See, e.g. Morrison et al., 1984, Proc. Natl. Acad. Sci., 81:6851–6855; Neuberger et al., 1984, Nature, 312:604–608; Takeda et al., 1985, Nature, 314:452–454. A variation of this approach is to replace residues outside the antigen-binding domains of a non-human antibody with the corresponding human sequences (see WO 94/11509). Another approach for production of human monoclonal antibodies is the use of xenogenic mice as described in U.S. Pat. No. 5,814,318, Lonberg et al. and U.S. Pat. No. 5,939, 598, Kucherlapati et al. These genetically engineered mice are capable of expressing certain unrearranged human heavy and light chain immunoglobulin genes, with their endogenous immunoglobulin genes being inactivated.

In addition, techniques have been developed for the generation of single chain antibodies (U.S. Pat. No. 4,946, 778, Ladner et al.; Bird, 1988, Science 242:423–426; Huston et al., 1988, *Proc. Natl. Acad. Sci. USA* 85:5879–5883; and Ward et al., 1989, Nature 341:544–546). Single chain antibodies are formed by linking the heavy and light chain fragments of the Fv region via an amino acid bridge, resulting in a single chain polypeptide.

The specificity of an antibody refers to the ability of the antibody to distinguish polypeptides comprising the immunizing epitope from other polypeptides. An ordinary skill in the art can readily determine without undue experimentation whether an antibody shares the same specificity as a antibody of this invention by determining whether the antibody being tested prevents an antibody of this invention from binding the polypeptide(s) with which the antibody is normally reactive. If the antibody being tested competes with the antibody of the invention as shown by a decrease in binding by the antibody of this invention, then it is likely that the two antibodies bind to the same or a closely related epitope. Alternatively, one can pre-incubate the antibody of this invention with the polypeptide(s) with which it is normally reactive, and determine if the antibody being tested is inhibited in its ability to bind the antigen. If the antibody being tested is inhibited, then, in all likelihood, it has the same, or a closely related, epitopic specificity as the antibody of this invention.

The antibodies of the invention can be bound to many different carriers. Accordingly, this invention also provides compositions containing antibodies and a carrier, which can be active or inert. Examples of well-known carriers include polypropylene, polystyrene, polyethylene, dextran, nylon, amylases, glass, natural and modified celluloses, polyacrylamides, agaroses and magnetite. The nature of the carrier can be either soluble or insoluble for purposes of the invention Those skilled in the art will know of other suitable carriers for binding antibodies, or will be able to ascertain such, using routine experimentation.

The antibodies of this invention can also be conjugated to a detectable agent or a hapten. The complex is useful to detect the polypeptide(s) containing the recognized epitopes to which the antibody specifically binds in a sample, using standard immunochemical techniques such as immunohistochemistry as described by Harlow and Lane (1988). supra. A wide diversity of labels and methods of labeling are known to those of ordinary skill in the art. Representative labels that can be employed in the present invention include radioisotopes, enzymes, colloidal metals, and luminescent compounds. Those of ordinary skill in the art will know of other suitable labels for binding to the antibody, or will be able to ascertain such, using routine experimentation.

The antibodies of the invention may be used, for example, in the detection of the GPCR in a biological sample and may, therefore, be utilized as part of a diagnostic or prognostic technique whereby patients may be tested for abnormal amounts of GPCR. Such antibodies may also be utilized in conjunction with, for example, compound screening schemes, as described below, for the evaluation of the effect of test compounds on expression and/or activity of the GPCR gene product. In addition, such antibodies can be used as therapeutics for restoring normal or inhibiting aberrant GPCR response in a cell.

Screening Assays for GPCR modulators

A wealth of studies has shown that GPCRs play a central role in a variety of physiological processes. Defects in various components of GPCR signal transduction pathways have been found to account for a vast number of diseases, including numerous forms of cancer, vascular diseases, metabolic diseases, immunological, and neuronal diseases. Indeed, modulators of GPCR response or activity have long been acknowledged as potential diagnostic and/or therapeutic agents.

Accordingly, the present invention provides a method for identifying a modulator of a GPCR encoded by the polynucleotide disclosed herein. The method involves the steps of (a) contacting a candidate GPCR modulator with said GPCR; and (b) assaying for an alteration in G protein response and/or GPCR expression.

For the purposes of this invention, a "modulator" is intended to include, but not be limited to biological or chemical molecules that interact with (e.g., bind to) GPCR (including, but not limited to the extracellular, cytoplasmic and transmembrane domains of GPCR), molecules that bind to intracellular proteins that interact with GPCR, molecules that interfere with the interaction of GPCR with transmembrane or intracellular proteins (e.g. heterotrimeric G proteins) involved in GPCR-mediated signal transduction, and molecules which modulate the activity of GPCR gene or expression profile. Of particular interest are modulators capable of binding to the extracellular domain of the GPCR and either mimic the activity triggered by the natural ligand (i.e., agonists) or inhibit the activity triggered by the natural ligand (i.e., antagonists), or "neutralize" the activity of the natural ligand. Also of particular significance are modulators interact with GPCR gene regulatory sequences (e.g., promoter sequences) so as to regulate GPCR gene expression (see, e.g. Platt, K. A., 1994, J. Biol. Chem. 269:28558–28562).

Candidate modulators for the present invention include a biological or chemical compound such as a simple or complex organic or inorganic molecule. Such compounds may include, but are not limited to, peptides such as, for example, soluble peptides, including but not limited to members of random peptide libraries; (see, e.g., Lam, K. S. et al., 1991, *Nature* 354:82–84; Houghten, R. et al., 1991, *Nature* 354:84–86), and combinatorial chemistry-derived molecular library made of D- and/or L-configuration amino acids, phosphopeptides (including, but not limited to, members of random or partially degenerate, directed phosphopeptide libraries; see, e.g., Songyang, Z. et al., 1993, Cell 72:767–778); molecules from natural product libraries, antibodies (including, but not limited to, polyclonal, monoclonal, humanized, anti-idiotypic, chimeric or single chain antibodies, and FAb, $F(ab')_2$ and FAb expression library fragments, and epitope-binding fragments thereof). In addition, a vast array of small organic or inorganic compounds from natural sources such as plant or animal extracts, and the like, can be employed in the screening assay. It should be understood, although not always explicitly stated that the modulator is used alone or in combination with another modulator, having the same or different biological activity as the modulators identified by the inventive screen.

While crude receptor signaling studies can be performed outside of cells using, for example, reconstituted vesicles (see, e.g., J. R. Hepler,J. Biol. Chem. 271: 496–504, 1996), it is preferable to employ cell-based functional assays. A preferred cell-based method for identifying GPCR modulators generally includes the following steps: (a) providing a host cell expressing, or preferably over-expressing a GPCR of interest; (b) exposing the cell to a candidate GPCR modulator, and (c) detecting an alteration in GPCR response or GPCR expression within the host cell.

Suitable conditions to allow binding of a modulator a GPCR are physiological conditions wherein the pH is maintained between 6 and 8, and the temperature is between about 20–40 degrees C. As used herein, the binding of a modulator to GPCR is understood to denote an interaction of the molecule with any portions of the GPCR polypeptide, which may result in a conformational change in topology of the receptor. The binding of the modulator to a GPCR polypeptide may either trigger (in the case of agonist) or block (in the case of antagonist) a detectable GPCR response. Such GPCR response includes but is not limited to (a) activation of phospholipase C proteins; (b) increase in phosphatidylinositol (PI) hydrolysis; (c) increase in intracellular calcium; (d) inhibition of the adenylyl cyclase activity; and (e) activation of adenylyl cyclase activity resulting in transient or more permanent accumulation of intracellular cAMP.

Methods of measuring intracellular inositol phosphates are well known in the art. Briefly, cell membrane phospholipids can be labeled by incubating host cells with [$^3$H] myo-inositol for 20–24 hours. Cells are then stimulated with appropriate modulators. Cell extracts can be collected and inositol phosphates separated by ion-exchange chromatography (e.g., by using AG1-X8 in either the chloride- or formate-form; when only $IP_3$ levels are to be determined, the chloride-form is preferably used, whereas the formate form can be used to resolve the major inositol phosphates ($IP_3$, $IP_2$ and $IP_1$).

Measuring intracellular calcium fluctuation can be rapidly accomplished with the use of calcium-sensitive fluorescent probes, including but not limited to Fura-2, Fluo-3 and Calcium Green-1. Changes of calcium level are reflected by a change in fluorescence of these probes, which can be measured by a high throughput assay that is adaptable to robotic processing. For example, host cells loaded with fluorescent probes can be monitored by FLIPR (Molecular Devices Corp.), an instrument capable of performing stimulation in all 96 wells of samples contained in a microplate simultaneously, and providing real-time measurement and functional data once every second. Typically, the assay is completed in less than fifteen minutes. Since more than a hundred 96-microplates can be read in a day, nearly 10,000 different compounds can be tested for GPCR agonist or antagonist. A variety of cell types, both adherent and non-adherent, can be used in FLIPR.

Another exemplary high throughput assay for measuring intracellular calcium or cAMP content involves induction of a reporter gene operatively linked to a calcium-responsive or cAMP-responsive element (e.g. promoter sequence). In this method, a calcium flux or cAMP accumulation resulting from the activation of GPCR turns on the promoter which subsequently drives the expression of a reporter gene encoding a protein with an enzymatic activity that can be easily detected, preferably by a colorimetric or fluorescent assay. Commonly used reporter proteins include: β-galactosidase, β-lactamase, chloramphenicol acetyltransferase (CAT), luciferase, green fluorescent protein (GFP) and its derivatives, among others. Reporter proteins can also be linked to other proteins whose expression is dependent upon the stimulation of GPCRs. An illustrative example would be a fusion protein comprising luciferase sequence in frame with the open-reading frame of nuclear factor of activated T cells (NFAT). Since the transcription of NFAT requires the co-activation of calcium and protein kinases C signaling pathways acting downstream of GPCRs, an effective coupling of heterotrimeric G protein to the receptors can then be measured by assaying NFAT-mediated luciferase activity (Boss et al., J. Biol. Chem., 271: 10429–10432, 1996). In practice of this method, a preferred host cell is one of lymphoid or neuronal origin, such as Jurkat cells and pheochromocytoma PC12 cells. However, the choice of host cells is not limited to these two types, as NFAT and NFAT isoforms are present in a variety of cells including endothelial and myeloid cells.

Other screening techniques include the use of cells which express the G-protein coupled receptor (for example, transfected CHO cells) in a system which measures extracellular pH changes caused by receptor activation. In addition, a cytosensor microphysiometer can be used to detect and monitor the response of cells to chemical substances as described in McConnell et al. (1992, Science 257: 1906–1912). For example, potential agonists or antagonists may be contacted with a cell which expresses the G protein-coupled receptor and a second messenger response, e.g., signal transduction or pH changes, may be measured to determine whether the potential agonist or antagonist is effective.

Yet another screening procedure involves the use of the melanophores which are transfected to express the G-protein coupled receptor of the present invention. Such a screening technique is described in PCT WO 92/01810.

Another such screening technique involves introducing RNA encoding GPCR into Xenopus oocytes to transiently express the receptor. The receptor expressing oocytes may then be contacted, in the case of antagonist screening, with the receptor ligand and a compound to be screened, followed by detection of inhibition of a calcium signal.

Screening for antagonists can also be carried out by a contacting a candidate antagonist in the presence of labeled ligands to cells which express the receptor on the surface. The amount of labeled ligand bound to the receptors is inversely proportional to the ability of the candidate antagonist to inhibit ligand binding. Thus, a reduced amount of labeled ligands bound to the receptor indicates that the antagonist is effective in inhibiting the binding of the natural ligand to the receptor.

A variety of in vitro assays are also available in the art to identify modulators of the present invention. In general, the in vitro assays are performed by contacting the GPCR polypeptide with a candidate modulator under conditions that will allow a complex to form between the receptor and the modulator. The formation of the complex can be detected directly or indirectly according standard procedures in the art. In the direct detection method, the modulators are supplied with a detectable label and unreacted modulators may be removed from the complex; the amount of remaining label thereby indicating the amount of complex formed. For such method, it is preferable to select labels that remain attached to the modulators even during stringent washing conditions. It is more important, however, that the label does not interfere with the binding reaction. In the alternative, an indirect detection procedure requires the modulators to contain a label introduced either chemically or enzymatically, that can be detected by affinity cytochemistry. A desirable label generally does not interfere with target binding or the stability of the resulting modulator-receptor complex. However, the label is typically designed to be accessible to an antibody for an effective binding and hence generating a detectable signal. A wide variety of labels are known in the art. Non-limiting examples of the types of labels which can be used in the present invention include radioisotopes, enzymes, colloidal metals, fluorescent compounds, bioluminescent compounds, and chemiluminescent compounds.

The amount of modulator-receptor complexes formed during the binding reaction can be quantified by standard quantitative assays. As illustrated above, the formation of modulator-receptor complex can be measured directly by the amount of label remained at the site of binding. In an alternative, the modulator is tested for its ability to compete with a labeled ligand for binding sites on the specific receptor. In this competitive assay, the amount of label captured is inversely proportional to the ability of the modulator to compete for receptor binding.

The competitive assay can also be employed for identifying modulators capable of interfering interactions between a GPCR polypeptide and downstream signaling molecules. These modulators are particularly useful in regulating the signaling events mediated by GPCR, and hence are potential therapeutics for restoring or down-regulating GPCR activity in a cell. Various competitive assay formats are well known in the art (e.g. heterogenous or homogenous assay systems), and hence are not detailed herein.

Modulators such as transmembrane proteins or intracellular proteins capable of interacting with GPCR can be identified by a vast diversity of in vitro or in vivo is techniques that are well established in the art Among the conventional methods are co-immunoprecipitation, crosslinking and co-purification through gradients or chromatographic columns of cell lysates or proteins obtained from cell lysates. For these assays, the GPCR component used can be a full length GPCR, a soluble derivative lacking the membrane-anchoring region, a peptide corresponding to one or more domains of the GPCR. Once isolated, such an intracellular protein can be identified and can, in turn, be used, in conjunction with standard techniques, to identify proteins with which it interacts. For example, at least a portion of the amino acid sequence of an intracellular protein which interacts with the GPCR can be ascertained using techniques well known to those of skill in the art, such as via the Edman degradation technique or other peptide mapping techniques.

In an alternative, GPCR interacting proteins can be isolated by yeast two hybrid system as illustrated by Chien et al., 1991, Proc. Natl. Acad. Sci. USA, 88:9578–9582. This hybrid system is also commercially available from Clontech (Palo Alto, Calif.).

In addition to compounds affecting GPCR activities or cellular responses, modulators capable of regulating the GPCR gene expression are also encompassed within this embodiment. Alteration of gene expression can be determined by examining the GPCR protein product or GPCR MnRNA level.

Determining the protein level involves a) providing a biological sample containing polypeptides; and (b) measuring the amount of any immunospecific binding that occurs between an antibody reactive to the protein products of interest and a component in the sample, in which the amount of immunospecific binding indicates the level of the protein products.

Biological samples used for this invention encompass body fluid, solid tissue samples, tissue cultures or cells derived therefrom and the progeny thereof, and sections of smears prepared from any of these sources.

A variety of techniques are available in the art for protein analysis. They include but are not limited to radioimmunoassays, ELISA (enzyme linked immunoradiometric assays), "sandwich" immunoassays, immunoradiometric assays, in situ immunoassays (using e.g., colloidal gold, enzyme or radioisotope labels), western blot analysis, immunoprecipitation assays, immunoflourescent assays, and SDS-PAGE. In addition, cell sorting analysis can be employed to detect cell surface antigens. Such analysis involves labeling target cells with antibodies coupled to a detectable agent, and then separating the labeled cells from the unlabeled ones in a cell sorter. A sophisticated cell separation method is fluorescence-activated cell sorting (FACS). Cells traveling in single file in a fine stream are passed through a laser beam, and the fluorescence of each cell bound by the fluorescently labeled antibodies is then measured.

Antibodies that specifically recognize and bind to the protein products of interest are required for conducting the aforementioned protein analyses. Anti-GPCR antibodies can be generated by the methods disclosed under the "Antibody section" or other methods well known in the art. See Harlow and Lane (1988) supra. and Sambrook et al. (1989) supra.

To determine a change in the GPCR MRNA level in a cell, hybridization assays employing the invention polynucleotides is generally performed. Nucleic acid contained in the aforementioned biological samples is first extracted according to standard methods in the art. For instance, mRNA can be isolated using various lytic enzymes or chemical solutions according to the procedures set forth in Sambrook et al. (1989), supra or extracted by nucleic-acid-binding resins following the accompanying instructions provided by manufactures. The MRNA contained in the extracted nucleic acid sample is then detected by hybridization (e.g. Northern blot analysis, gene chip assays as described in U.S. Pat. No. 5,445,934, Fodor et al.) and/or amplification procedures according to methods widely known in the art or based on the methods disclosed herein.

Diagnostics and therapeutics of the present invention

The polynucleotides, polypeptides, antibodies, and modulators of this invention provide specific reagents that can be used in standard diagnostic, or prognostic evaluation of cadiovascular, neuronal, metabolic, and immunological disorders. These reagents may be used, for example, for (a) the detection of the presence of GPCR gene mutations, or the detection of differential expression of GPCR mRNA or protein product relative to the nondisorder state; (b) the detection of perturbations or abnormalities in the signal transduction pathway mediated by GPCR. Techniques for genetic analyses and protein analyses are described in the sections above. Provided with these critical reagents for detecting the GPCR polynucleotides and polypeptides, one skilled in the art can readily perform various diagnostic procedures without undue experimentation. Where desired, a normal or standard GPCR expression profile or activity range can be established for a comparative diagnosis.

The polynucleotides, polypeptides, antibodies, and modulators of this invention may be employed as therapeutics for treatment of GPCR associated diseases. Based on the chemical and structural homology among the invention GPCRs and previously characterized GPCRs including various members of the Family 2B GPCRs, GPCR of this invention is expected to play a role in the regulation of a variety of biological pathways involving e.g. ion channel (e.g. calcium channel), protein kinases, proteases and many other second messengers in a cell. Dysfunction of these cellular components have been found to account for a vast number of diseases, including numerous forms of cancer, diabetes and other pancreatic diseases, osteoporosis, immunological, vascular diseases, neuronal diseases, hypercalcemia, and hypreparathyroid Accordingly, in one aspect, GPCR anti-sense polynucleotides can be administered to a subject to treat a disease correlated with an abnormally high level of GPCR expression. Conversely, sense-strand GPCR can be delivered to and expressed in a subject suffering from a disease correlated with an aberrantly low level of GPCR expression.

In another aspect, GPCR polypeptides, antibodies, antigen-binding fragments, and modulators that function as agonists can be administered to stimulate the endogenous GPCR activity where such a stimulation is appropriate.

In another aspect, GPCR polypeptides, antibodies, antigen-binding fragments, and modulators that function as antagonists can be administered to a subject exhibiting an abnormal high level of endogenous GPCR activity.

The present invention encompasses pharmaceutical compositions and containing GPCR polynucleotides, polypeptides, vectors, modulators, antibodies, fragments thereof, and/or cell lines which produce the antibodies or fragments. Such pharmaceutical compositions are useful for eliciting an immune response and treating GPCR associated diseases, either alone or in conjunction with other forms of therapy, such as chemotherapy or radiotherapy.

The preparation of pharmaceutical compositions of this invention is conducted in accordance with generally accepted procedures for the preparation of pharmaceutical preparations. See, for example, *Remington's Pharmaceutical Sciences* 18*th Edition* (1990), E. W. Martin ed., Mack Publishing Co., PA. Depending on the intended use and mode of administration, it may be desirable to process the active ingredient further in the preparation of pharmaceutical compositions. Appropriate processing may include sterilizing, mixing with appropriate non-toxic and non-interfering components, dividing into dose units, and enclosing in a delivery device.

Liquid pharmaceutically acceptable compositions can, for example, be prepared by dissolving or dispersing a polypeptide embodied herein in a liquid excipient, such as water, saline, aqueous dextrose, glycerol, or ethanol. The composition can also contain other medicinal agents, pharmaceutical agents, adjuvants, carriers, and auxiliary substances such as wetting or emulsifying agents, and pH buffering agents.

Pharmaceutical compositions of the present invention are administered by a mode appropriate for the form of composition. Typical routes include subcutaneous, intramuscular, intraperitoneal, intradermal, oral, intranasal, and intrapulmonary (i.e., by aerosol). Pharmaceutical compositions of this invention for human use are typically administered by a parenteral route, most typically intracutancous, subcutaneous, or intramuscular.

Pharmaceutical compositions for oral, intranasal, or topical administration can be supplied in solid, semi-solid or liquid forms, including tablets, capsules, powders, liquids, and suspensions. Compositions for injection can be supplied as liquid solutions or suspensions, as emulsions, or as solid forms suitable for dissolution or suspension in liquid prior to injection. For administration via the respiratory tract, a preferred composition is one that provides a solid, powder, or liquid aerosol when used with an appropriate aerosolizer device. Although not required, pharmaceutical compositions are preferably supplied in unit dosage form suitable for administration of a precise amount. Also contemplated by this invention are slow release or sustained release forms, whereby a relatively consistent level of the active compound are provided over an extended period.

Kits comprising the polynucleotides of the present invention

The present invention also encompasses kits containing the polynucleotides, polypeptides, antibodies, antigen-binding fragments and vectors of this invention in suitable packaging. Kits embodied by this invention include those that allow someone to detect the presence or quantify the amount of GPCR polynucleotide or polypeptide that is suspected to be present in a sample. The sample is optionally pre-treated for enrichment of the target being tested for. The user than applies a reagent contained in the kit in order to detect the changed level or alteration in the diagnostic component.

Each kit necessarily comprises the reagent which renders the procedure specific: a reagent antibody or polynucleotide probe or primer, used for detecting target protein and polynucleotide, respectively. Each reagent can be supplied in a solid form or dissolved/suspended in a liquid buffer suitable for inventory storage, and later for exchange or addition into the reaction medium when the test is performed. Suitable packaging is provided. The kit can optionally provide additional components that are useful in the procedure. These optional components include, but are not limited to, buffers, capture reagents, developing reagents, labels, reacting surfaces, means for detection, control samples, instructions, and interpretive information. The kits can be employed to test a variety of biological samples, including body fluid, solid tissue samples, tissue cultures or cells derived therefrom and the progeny thereof, and sections or smears prepared from any of these sources. Diagnostic procedures using the antibodies of this invention can be performed by diagnostic laboratories, experimental laboratories, practitioners, or private individuals.

Computer-readable Media of the Present Invention

The present invention provides a computer readable medium having recorded the polynucleotide and/or polypeptides of the present invention. As used herein, a "computer readable medium" refers to any medium which can be read and accessed directly by a computer. Such media include, but are not limited to magnetic storage media, such as floppy discs, hard disc storage medium, and magnetic tape; optical storage media such as CD-ROM; electrical storage media such as RAM and ROM; and hybrids of these categories, such as magnetic/optical storage media. A skilled artisan can readily appreciate how any of the presently known computer readable mediums can be used to create a manufacture comprising compute readable medium having recorded thereon the polynucleotides and/or polypeptides of the present invention. Likewise, it will be clear to those of skill how additional computer readable media that may be developed also can be used to create analogous manufactures having recorded thereon the invention polynucleotides and/or polypeptides encoded thereby.

The term "recorded" refers to a process for storing information on computer readable medium. A skilled artisan can readily adopt any of the presently know methods for recording information on computer readable medium to generate manufactures comprising polynucleotides or polypeptides of the present invention. A variety of data storage structures are available to a skilled artisan for creating a computer readable medium having recorded thereon the nucleotide or amino acid sequence information of this invention. The choice of the data storage structure will generally be based on the means chosen to access the stored information. In addition, a variety of data processor programs and formats can be used to store the sequence information of the present invention on a computer readable medium. For instance, the sequence information can be stored in a file using ASCII or other binary formats. Where desired, files stored under ASCII format can be subcategorized into comma delimited file, tab delimited file, space delimited file, and the like. Non-limiting exemplary binary formats other than ASCII include Microsoft Word, Word Perfect, Excel, and Adobe Acrobat. In addition, the sequence formation can be stored in certain database format including but not limited to DB2, Sybase, Oracle, Informix, SQL or the like. A skilled artisan can readily adapt any number of data-processing software formats in order to obtain computer readable medium having recorded thereon the sequence information of the present invention.

Additional References:

1. Gastroenterology 1998 February; 114(2):382–97 "Secretin and vasoactive intestinal peptide receptors: members of a unique family of G protein-coupled receptors" by Ulrich C D 2nd, Holtmann M, Miller L J 2. Ann N Y Acad Sci 1996 December 26;805:172–81; discussion 181-3 "Speculations on the mechanism of hormone-receptor interactions of the secretin/glucagon family of polypeptide hormones derived from computational structural studies" by Momany F A, Bowers C Y 3. Ann N Y Acad Sci 1996 December 26;805:94–109; discussion 110-1 "Receptors for VIP, PACAP, secretin, GRF, glucagon, GLP-1, and other members of their new family of G protein-linked receptors: structure-function relationship with special reference to the human VIP- I receptor" by Laburthe M, Couvineau A, Gaudin P, Maoret J J, Rouyer-Fessard C, Nicole P 4. Ann N Y Acad Sci 1996 December 26;805:44–51; discussion 52-3 "PACAP/VIP receptors in pancreatic beta-cells: their roles in insulin secretion" by Inagaki N, Kuromi H, Seino S 5. Nippon Rinsho 1996 April;54(4):1078–82 "Gastric inhibitory polypeptide (GIP) and GIP receptor" by Yasuda K, Seino Y 6. Eur J Endocrinol 1995 July;133(1): 17–20 "Calcitonin, calcitonin gene-related peptide, adrenomedullin and amylin: homologous peptides, separate receptors and overlapping biological actions" by Muff R, Born W, Fischer J A 7. Neurosci Biobehav Rev 1995 Summer,19(2):251–9 "Role of VIP in the regulation of LH secretion in the female rat" by Weick R F, Stobie K M 8. http://www.expasy.ch/cgi-bin/lists?7tmrlist.txt, Swiss Institute of Bioinformatics and University of Geneva, Switzerland (2000) "List of 7-transmembrane G-linked receptor sequences" by Bairoch 9. Genome Research 2000, 10(4):529–538 "Genie-Gene finding in Drosophila melanogaster" by Reese, M. G., Kulp, D., Tammana, H., Haussler, D 10. Proc. Conf. on Intelligent Systems for Molecular Biology ('96) 134–142, St. Louis, Mo., A Press "Ageneralized hidden Markov model for the recognition of human genes inDNA" edited by D. J. States, P. Agarwal, T. Gaasterland, L Hunter and R. Smith, Kulp, D., Haussler, D., Reese, M. G., and Eeckman, F. H.

11. Channels and Transporters, 2(1):1–7 (1994) "GCRDb: A G protein-coupled receptor database, Receptors and Channels: The International Journal of Receptors." by L. F. Kolakowski, 12. J. Mol. Biol.215:403–410 (1990) "Basic local alignment search tool" by Altschul, S. F., Gish, W., Miller, W., Myers, E. W. & Lipman, D. J.

SEQUENCE LISTING

```
<160> NUMBER OF SEQ ID NOS: 20

<210> SEQ ID NO 1
<211> LENGTH: 274
<212> TYPE: PRT
<213> ORGANISM: Artificial Sequence
<220> FEATURE:
<223> OTHER INFORMATION: Synthetic Organism
<220> FEATURE:
<221> NAME/KEY: misc_feature
<222> LOCATION: (126)..(126)
<223> OTHER INFORMATION: Xaa can be any naturally occurring amino acid
<220> FEATURE:
<221> NAME/KEY: misc_feature
<222> LOCATION: (146)..(146)
<223> OTHER INFORMATION: Xaa can be any naturally occurring amino acid

<400> SEQUENCE: 1

Leu Leu Ala Pro Thr Gly Ser Leu Phe Arg Asn Cys Thr Gln Asp Gly
1               5                   10                  15

Trp Ser Glu Thr Phe Pro Arg Pro Asn Leu Ala Cys Gly Val Asn Val
            20                  25                  30

Asn Asp Ser Ser Asn Glu Lys Arg Ser Tyr Leu Leu Lys Leu Lys Val
        35                  40                  45

Met Tyr Thr Val Gly Tyr Ser Ser Ser Leu Val Met Leu Leu Val Ala
    50                  55                  60

Leu Gly Ile Leu Cys Ala Phe Arg Arg Leu His Cys Thr Arg Asn Tyr
65                  70                  75                  80

Ile His Met His Leu Phe Val Ser Phe Ile Leu Arg Ala Leu Ser Asn
                85                  90                  95

Phe Ile Lys Asp Ala Val Leu Phe Ser Ser Asp Asp Val Thr Tyr Cys
            100                 105                 110

Asp Ala His Arg Gly Cys Lys Leu Val Met Val Leu Phe Xaa Tyr Cys
        115                 120                 125

Ile Met Ala Asn Tyr Ser Trp Leu Leu Val Glu Gly Ser Thr Phe Thr
    130                 135                 140

His Xaa Leu Ala Ile Ser Phe Phe Ser Glu Arg Lys Tyr Leu Gln Gly
145                 150                 155                 160

Phe Val Ala Phe Gly Trp Gly Ser Pro Ala Ile Phe Val Ala Leu Trp
                165                 170                 175

Ala Ile Ala Arg His Phe Leu Glu Asp Val Gly Cys Trp Asp Ile Asn
            180                 185                 190

Ala Asn Ala Ser Ile Trp Trp Ile Ile Arg Gly Pro Val Ile Leu Ser
        195                 200                 205

Ile Leu Asn Phe Ile Leu Phe Ile Asn Ile Leu Arg Ile Leu Met Arg
    210                 215                 220
```

-continued

```
Lys Leu Arg Thr Gln Glu Thr Arg Gly Asn Glu Val Ser His Tyr Lys
225                 230                 235                 240

Arg Leu Ala Arg Ser Thr Leu Leu Leu Ile Pro Leu Phe Gly Ile His
                245                 250                 255

Tyr Ile Val Phe Ala Phe Ser Pro Glu Asp Ala Met Glu Ile Gln Leu
            260                 265                 270

Phe Phe


<210> SEQ ID NO 2
<211> LENGTH: 381
<212> TYPE: DNA
<213> ORGANISM: Artificial Sequence
<220> FEATURE:
<223> OTHER INFORMATION: Synthetic Organism

<400> SEQUENCE: 2

ctcttggcac ccacaggttc cttgttccga aactgcacac aggatggctg gtcagaaacc     60

ttccccaggc ctaatctggc ctgtggcgtt aatgtgaacg actcttccaa cgagaagcgg    120

cactcctacc tgctgaagct gaaagtcatg tacaccgtgg gctacagctc ctccctggtc    180

atgctcctgg tcgcccttgg catcctctgt gctttccgga ggctccactg cactcgcaac    240

tacatccaca tgcacctgtt cgtgtccttc atccttcgtg ccctgtccaa cttcatcaag    300

gacgccgtgc tcttctcctc agatgatgtc acctactgcg atgcccacag ggcgggctgc    360

aagctggtca tggtgctgtt c                                              381


<210> SEQ ID NO 3
<211> LENGTH: 447
<212> TYPE: DNA
<213> ORGANISM: Artificial Sequence
<220> FEATURE:
<223> OTHER INFORMATION: Synthetic Organism
<220> FEATURE:
<221> NAME/KEY: misc_feature
<222> LOCATION: (58)..(58)
<223> OTHER INFORMATION: n is a, c, g, or t

<400> SEQUENCE: 3

tactgcatca tggccaacta ctcctggctg ctggtggaag gctctacctt cacacatntc     60

ctcgccatct ccttcttctc tgaaagaaag tacctccagg gatttgtggc attcggatgg    120

ggttctccag ccatttttgt tgctttgtgg gctattgcca gacactttct ggaagatgtt    180

gggtgctggg acatcaatgc caacgcatcc atctggtgga tcattcgtgg tcctgtgatc    240

ctctccatcc tgattaattt catccttttc ataaacattc taagaatcct gatgagaaaa    300

cttagaaccc aagaaacaag aggaaatgaa gtcagccatt ataagcgcct ggccaggtcc    360

actctcctgc tgatccccct ctttggcatc cactacatcg tcttcgcctt ctccccagag    420

gacgctatgg agatccagct gtttttt                                        447


<210> SEQ ID NO 4
<211> LENGTH: 828
<212> TYPE: DNA
<213> ORGANISM: Artificial Sequence
<220> FEATURE:
<223> OTHER INFORMATION: Synthetic Organism
<220> FEATURE:
<221> NAME/KEY: misc_feature
<222> LOCATION: (439)..(439)
<223> OTHER INFORMATION: n is a, c, g, or t

<400> SEQUENCE: 4
```

-continued

```
ctcttggcac ccacaggttc cttgttccga aactgcacac aggatggctg gtcagaaacc     60

ttccccaggc ctaatctggc ctgtggcgtt aatgtgaacg actcttccaa cgagaagcgg    120

cactcctacc tgctgaagct gaaagtcatg tacaccgtgg gctacagctc ctccctggtc    180

atgctcctgg tcgcccttgg catcctctgt gctttccgga ggctccactg cactcgcaac    240

tacatccaca tgcacctgtt cgtgtccttc atccttcgtg ccctgtccaa cttcatcaag    300

gacgccgtgc tcttctcctc agatgatgtc acctactgcg atgcccacag ggcgggctgc    360

aagctggtca tggtgctgtt ctactgcatc atggccaact actcctggct gctggtggaa    420

ggctctacct tcacacatnt cctcgccatc tccttcttct ctgaaagaaa gtacctccag    480

ggatttgtgg cattcggatg gggttctcca gccatttttg ttgctttgtg ggctattgcc    540

agacactttc tggaagatgt tgggtgctgg gacatcaatg ccaacgcatc catctggtgg    600

atcattcgtg gtcctgtgat cctctccatc ctgattaatt tcatcctttt cataaacatt    660

ctaagaatcc tgatgagaaa acttagaacc caagaaacaa gaggaaatga agtcagccat    720

tataagcgcc tggccaggtc cactctcctg ctgatccccc tctttggcat ccactacatc    780

gtcttcgcct tctccccaga ggacgctatg gagatccagc tgtttttt                 828
```

```
<210> SEQ ID NO 5
<211> LENGTH: 320
<212> TYPE: PRT
<213> ORGANISM: Artificial Sequence
<220> FEATURE:
<223> OTHER INFORMATION: Synthetic Organism

<400> SEQUENCE: 5

Pro Thr Phe Ile Leu Phe Ser Phe Gln Pro Gly Asp Lys Arg Thr Lys
1               5                   10                  15

His Ile Cys Val Tyr Trp Glu Gly Ser Glu Gly Gly His Trp Ser Thr
            20                  25                  30

Glu Gly Cys Ser His Val His Ser Asn Gly Ser Tyr Thr Lys Cys Lys
        35                  40                  45

Cys Phe His Leu Ser Ser Phe Ala Val Leu Val Ala Leu Ala Pro Lys
    50                  55                  60

Asp Pro Val Leu Thr Val Ile Thr Gln Val Gly Leu Thr Ile Ser Leu
65                  70                  75                  80

Leu Cys Leu Phe Leu Ala Ile Leu Thr Phe Leu Leu Cys Arg Pro Ile
                85                  90                  95

Gln Asn Thr Ser Thr Ser Leu His Leu Glu Leu Ser Leu Cys Leu Phe
            100                 105                 110

Leu Ala His Leu Leu Phe Leu Thr Gly Ile Asn Arg Thr Glu Pro Glu
        115                 120                 125

Leu Cys Ser Ile Ile Ala Gly Leu Leu His Phe Leu Tyr Leu Ala Cys
    130                 135                 140

Phe Thr Trp Met Leu Leu Glu Gly Leu His Leu Phe Leu Thr Val Arg
145                 150                 155                 160

Asn Leu Lys Val Ala Asn Tyr Thr Ser Thr Gly Arg Phe Lys Lys Arg
                165                 170                 175

Phe Met Tyr Pro Val Gly Tyr Gly Ile Pro Ala Val Ile Ile Ala Val
            180                 185                 190

Ser Ala Ile Val Gly Pro Gln Asn Tyr Gly Thr Phe Thr His Cys Trp
        195                 200                 205

Leu Lys Leu Asp Lys Gly Phe Ile Trp Ser Phe Met Gly Pro Val Ala
```

-continued

```
    210                 215                 220

Val Ile Ile Leu Asn Leu Val Phe Tyr Phe Gln Val Leu Trp Ile Leu
225                 230                 235                 240

Arg Ser Lys Leu Ser Ser Leu Asn Lys Glu Val Ser Thr Ile Gln Asp
                245                 250                 255

Thr Arg Val Met Thr Phe Lys Ala Ile Ser Gln Leu Phe Ile Leu Gly
            260                 265                 270

Cys Ser Trp Gly Leu Gly Phe Phe Met Val Glu Glu Val Gly Lys Thr
        275                 280                 285

Ile Gly Ser Ile Ile Ala Tyr Ser Phe Thr Ile Ile Asn Thr Leu Gln
    290                 295                 300

Gly Val Leu Leu Phe Val Val His Cys Leu Leu Asn Arg Gln Val Arg
305                 310                 315                 320


<210> SEQ ID NO 6
<211> LENGTH: 969
<212> TYPE: DNA
<213> ORGANISM: Artificial Sequence
<220> FEATURE:
<223> OTHER INFORMATION: Synthetic Organism

<400> SEQUENCE: 6

cccactttca tactattctc tttccagcct ggtgacaaga gaacaaaaca tatctgtgtc     60

tactgggagg gatcagaggg aggccactgg tccacggagg gctgctctca tgtgcacagc    120

aacggttctt acaccaaatg caagtgcttc catctgtcca gctttgccgt cctcgtggct    180

cttgccccca aggaggaccc tgtgctgacc gtgatcaccc aggtggggct gaccatctct    240

ctgctgtgcc tcttcctggc catcctcacc ttcctcctgt gccggcccat ccagaacacc    300

agcacctccc tccatctaga gctctccctc tgcctcttcc tggcccacct cctgttcctg    360

acgggcatca acagaactga gcctgaggtg ctgtgctcca tcattgcagg gctgctgcac    420

ttcctctacc tggcttgctt cacctggatg ctcctggaag ggctgcacct cttcctcacc    480

gtcaggaacc tcaaggtggc caactacacc agcacgggca gattcaagaa gaggttcatg    540

taccctgtag gctacgggat cccagctgtg attattgctg tgtcagcaat agttggaccc    600

cagaattatg gaacatttac tcactgttgg ctcaagcttg ataaaggatt catctggagc    660

ttcatggggc cagtagcagt cattatcttg ataaacctgg tgttctactt ccaagttctg    720

tggattttga gaagcaaact ttcctccctc aataaagaag tttccaccat tcaggacacc    780

agagtcatga catttaaagc catttctcag ctatttatcc tgggctgttc ttggggcctt    840

ggtttttta tggttgaaga agtagggaag acgattggat caatcattgc atactcattc    900

accatcatca acacccttca gggagtgttg ctctttgtgg tacactgtct ccttaatcgc    960

caggtaagg                                                            969


<210> SEQ ID NO 7
<211> LENGTH: 217
<212> TYPE: PRT
<213> ORGANISM: Artificial Sequence
<220> FEATURE:
<223> OTHER INFORMATION: Synthetic Organism

<400> SEQUENCE: 7

Gln His Ser Asp Ala Val His Asp Leu Leu Leu Asp Val Ile Thr Trp
1               5                   10                  15

Val Gly Ile Leu Leu Ser Leu Val Cys Leu Leu Ile Cys Ile Phe Thr
            20                  25                  30
```

-continued

```
Phe Cys Phe Phe Arg Gly Leu Gln Ser Asp Arg Asn Thr Ile His Lys
        35                  40                  45

Asn Leu Cys Ile Ser Leu Phe Val Ala Glu Leu Leu Phe Leu Ile Gly
    50                  55                  60

Ile Asn Arg Thr Asp Gln Pro Ala Cys Ala Val Phe Ala Ala Leu Leu
65                  70                  75                  80

His Phe Phe Phe Leu Ala Ala Phe Thr Trp Met Phe Leu Glu Gly Val
                85                  90                  95

Gln Leu Tyr Ile Met Leu Val Glu Val Phe Glu Ser Glu His Ser Arg
            100                 105                 110

Arg Lys Tyr Phe Tyr Leu Val Gly Tyr Gly Met Pro Ala Leu Ile Val
        115                 120                 125

Ala Val Ser Ala Ala Val Asp Tyr Arg Ser Tyr Gly Thr Asp Lys Val
    130                 135                 140

Cys Trp Leu Arg Leu Asp Thr Tyr Phe Ile Trp Ser Phe Ile Gly Pro
145                 150                 155                 160

Ala Thr Leu Ile Ile Met Asn Val Ile Phe Leu Gly Ile Ala Leu Tyr
                165                 170                 175

Lys Met Phe His His Thr Ala Ile Leu Lys Pro Glu Ser Gly Cys Leu
            180                 185                 190

Asp Asn Ile Lys Leu Lys Ile Asn Ile Pro Ile Ile Lys Ser Ile Tyr
        195                 200                 205

Ile Tyr Met Tyr Ile Cys Met Cys Val
    210                 215


<210> SEQ ID NO 8
<211> LENGTH: 657
<212> TYPE: DNA
<213> ORGANISM: Artificial Sequence
<220> FEATURE:
<223> OTHER INFORMATION: Synthetic Organism

<400> SEQUENCE: 8

cagcacagtg atgcggtcca tgacctcctt ctggatgtga tcacgtgggt tggaattttg     60

ctgtcccttg tttgtctcct gatttgcatc ttcacatttt gctttttccg ggggctccag    120

agtgaccgta acaccatcca caagaacctc tgcatcagtc tctttgtagc agagctgctc    180

ttcctgattg ggatcaaccg aactgaccaa ccaattgcct gtgctgtttt cgctgccctg    240

ttacatttct tcttcttggc tgccttcacc tggatgttcc tggagggggt gcagctttat    300

atcatgctgg tggaggtttt tgagagtgaa cattcacgta ggaaatactt ttatctggtc    360

ggctatggga tgcctgcact cattgtggct gtgtcagctg cagtagacta caggagttat    420

ggaacagata aagtatgttg gctccgactt gacacctact tcatttggag ttttatagga    480

ccagcaactt tgataattat gcttaatgta atcttccttg ggattgcttt atataaaatg    540

tttcatcata ctgctatact gaaacctgaa tcaggctgtc ttgataacat caagttaaaa    600

attaatattc caattataaa atctatttat atctatatgt atatatgcat gtgtgtg       657


<210> SEQ ID NO 9
<211> LENGTH: 304
<212> TYPE: PRT
<213> ORGANISM: Artificial Sequence
<220> FEATURE:
<223> OTHER INFORMATION: Synthetic Organism

<400> SEQUENCE: 9
```

-continued

```
Gly Asn Val Ala Val Ala Phe Val Tyr Tyr Lys Ser Ile Gly Pro Leu
1               5                   10                  15

Leu Ser Ser Ser Asp Asn Phe Leu Leu Lys Pro Gln Asn Tyr Asp Asn
            20                  25                  30

Ser Glu Glu Glu Glu Arg Val Ile Ser Ser Val Ile Ser Val Ser Met
        35                  40                  45

Ser Ser Asn Pro Pro Thr Leu Tyr Glu Leu Glu Lys Ile Thr Phe Thr
    50                  55                  60

Leu Ser His Arg Lys Thr Asp Arg Tyr Arg Ser Leu Cys Ala Phe Trp
65                  70                  75                  80

Asn Tyr Ser Pro Asp Thr Met Asn Gly Ser Trp Ser Ser Glu Gly Cys
                85                  90                  95

Glu Leu Thr Tyr Ser Asn Glu Thr His Thr Ser Cys Arg Cys Asn His
            100                 105                 110

Leu Thr His Phe Ala Ile Leu Met Ser Ser Gly Pro Ser Ile Ile Lys
        115                 120                 125

Asp Tyr Asn Ile Leu Thr Arg Ile Thr Gln Leu Gly Ile Ile Ile Ser
    130                 135                 140

Leu Ile Cys Leu Ala Ile Cys Ile Phe Thr Phe Trp Phe Phe Ser Glu
145                 150                 155                 160

Ile Gln Ser Thr Arg Thr Thr Ile His Lys Asn Leu Cys Cys Ser Leu
                165                 170                 175

Phe Leu Ala Glu Leu Val Phe Leu Val Gly Ile Asn Thr Asn Thr Asn
            180                 185                 190

Lys Phe Cys Ser Ile Ile Ala Gly Leu Leu His Tyr Phe Phe Leu Ala
        195                 200                 205

Ala Phe Ala Trp Met Cys Ile Glu Gly Ile His Leu Tyr Leu Ile Val
    210                 215                 220

Val Gly Val Ile Tyr Asn Lys Gly Phe Leu His Lys Asn Phe Tyr Ile
225                 230                 235                 240

Phe Gly Tyr Leu Ser Pro Ala Val Val Val Gly Phe Ser Ala Ala Leu
                245                 250                 255

Gly Tyr Arg Tyr Tyr Gly Thr Thr Lys Val Cys Trp Leu Ser Thr Glu
            260                 265                 270

Asn Asn Phe Ile Trp Ser Phe Ile Gly Pro Ala Cys Leu Ile Ile Leu
        275                 280                 285

Val Cys Ile Tyr Lys Ile Val Ile Thr Ile Gln Lys Ser Asp Asp His
    290                 295                 300


<210> SEQ ID NO 10
<211> LENGTH: 921
<212> TYPE: DNA
<213> ORGANISM: Artificial Sequence
<220> FEATURE:
<223> OTHER INFORMATION: Synthetic Organism

<400> SEQUENCE: 10

ggcaatgttg cagttgcatt tgtatattat aagagtattg gtcctttgct ttcatcatct      60

gacaacttct tattgaaacc tcaaaattat gataattctg aagaggagga aagagtcata     120

tcttcagtaa tttcagtctc aatgagctca aacccaccca cattatatga acttgaaaaa     180

ataacattta cattaagtca tcgaaaggtc acagataggt ataggagtct atgtgcattt     240

tggaattact cacctgatac catgaatggc agctggtctt cagagggctg tgagctgaca     300

tactcaaatg agacccacac ctcatgccgc tgtaatcacc tgacacattt tgcaattttg     360
```

-continued

```
atgtcctctg gtccttccat tggtattaaa gattataata ttcttacaag gatcactcaa    420

ctaggaataa ttatttcact gatttgtctt gccatatgca tttttacctt ctggttcttc    480

agtgaaattc aaagcaccag gacaacaatt cacaaaaatc tttgctgtag cctatttctt    540

gctgaacttg tttttcttgt tgggatcaat acaaatacta ataagctctt ctgttcaatc    600

attgccggac tgctacacta cttcttttta gctgcttttg catggatgtg cattgaaggc    660

atacatctct atctcattgt tgtgggtgtc atctacaaca agggattttt gcacaagaat    720

ttttatatct ttggctatct aagcccagcc gtggtagttg gattttcggc agcactagga    780

tacagatatt atggcacaac caaagtatgt tggcttagca ccgaaaacaa ctttatttgg    840

agttttatag gaccagcatg cctaatcatt cttgtatgta tatataaaat tgttattaca    900

attcaaaaaa gtgatgatca t                                              921
```

<210> SEQ ID NO 11
<211> LENGTH: 203
<212> TYPE: PRT
<213> ORGANISM: Artificial Sequence
<220> FEATURE:
<223> OTHER INFORMATION: Synthetic Organism

<400> SEQUENCE: 11

```
Gly Ala Trp Ala Thr Thr Gly Cys Ser Val Ala Ala Leu Tyr Leu Asp
1               5                   10                  15

Ser Thr Ala Cys Phe Cys Asn His Ser Thr Ser Phe Ala Ile Leu Leu
            20                  25                  30

Gln Ile Tyr Glu Val Gln Gly Pro Glu Glu Glu Ser Leu Leu Arg Thr
        35                  40                  45

Leu Ser Phe Val Gly Cys Gly Val Ser Phe Cys Ala Leu Thr Thr Thr
    50                  55                  60

Phe Leu Leu Phe Leu Val Ala Gly Val Pro Lys Ser Glu Arg Thr Thr
65                  70                  75                  80

Val His Lys Asn Leu Thr Phe Ser Leu Ala Ser Ala Glu Gly Phe Leu
                85                  90                  95

Met Thr Ser Glu Trp Ala Lys Ala Asn Glu Ala Cys Val Ala Val Thr
            100                 105                 110

Val Ala Met His Phe Leu Phe Leu Val Ala Phe Ser Trp Met Leu Val
        115                 120                 125

Glu Gly Leu Leu Leu Trp Arg Lys Val Val Ala Val Ser Met His Pro
    130                 135                 140

Gly Pro Gly Met Arg Leu Tyr His Ala Thr Gly Trp Gly Val Pro Val
145                 150                 155                 160

Gly Ile Val Ala Val Thr Leu Ala Met Leu Pro His Asp Tyr Val Ala
                165                 170                 175

Pro Gly His Cys Trp Leu Asn Val His Thr Asn Ala Ile Trp Ala Phe
            180                 185                 190

Val Gly Pro Val Leu Phe Val Leu Thr Val Ser
        195                 200
```

<210> SEQ ID NO 12
<211> LENGTH: 615
<212> TYPE: DNA
<213> ORGANISM: Artificial Sequence
<220> FEATURE:
<223> OTHER INFORMATION: Synthetic Organism

<400> SEQUENCE: 12

-continued

```
ggtgcctggg ccaccacagg ctgctccgtg gctgccctgt acctggactc caccgcctgc     60

ttctgcaacc acagcaccag ctttgccatc ctgctgcaaa tctatgaagt acagagaggc    120

cctgaggagg agtcgctgct gaggactctg tcatttgtgg gctgtggcgt gtccttctgc    180

gccctcacca ccaccttctt gctcttcctg gtggccgggg tccccaagtc agagcgaacc    240

acagtccaca agaacctcac cttctccctg gcctctgccg agggcttcct catgaccagc    300

gagtgggcca aggccaatga ggtggcatgt gtggctgtca cagtcgcaat gcacttcctc    360

tttctggtgg cattctcctg gatgctggtg gaggggctgc tgctgtggag gaaggtggta    420

gctgtgagca tgcacccggg cccaggcatg cggctctacc acgccacagg ctggggcgtg    480

cctgtgggca tcgtggcggt caccctggcc atgctccccc atgactacgt ggcccccgga    540

cattgctggc tcaatgtgca cacaaatgcc atctgggcct tcgtggggcc tgtgctcttc    600

gtgctgactg tgagc                                                     615
```

<210> SEQ ID NO 13
<211> LENGTH: 1339
<212> TYPE: PRT
<213> ORGANISM: Artificial Sequence
<220> FEATURE:
<223> OTHER INFORMATION: Synthetic Organism

<400> SEQUENCE: 13

```
Met Lys Ser Pro Arg Arg Thr Thr Leu Cys Leu Met Phe Ile Val Ile
1               5                   10                  15

Tyr Ser Ser Lys Ala Ala Leu Asn Trp Asn Tyr Glu Ser Thr Ile His
            20                  25                  30

Pro Leu Leu His Glu His Glu Pro Ala Gly Glu Glu Ala Leu Arg Gln
        35                  40                  45

Lys Arg Ala Val Ala Thr Lys Ser Pro Thr Ala Glu Glu Tyr Thr Val
    50                  55                  60

Asn Ile Glu Ile Ser Phe Glu Asn Ala Ser Phe Leu Asp Pro Ile Lys
65                  70                  75                  80

Ala Tyr Leu Asn Ser Leu Ser Phe Pro Ile His Gly Asn Asn Thr Asp
                85                  90                  95

Gln Ile Thr Asp Ile Leu Ser Ile Asn Val Thr Thr Val Cys Arg Pro
            100                 105                 110

Ala Gly Asn Glu Ile Trp Cys Ser Cys Glu Thr Gly Tyr Gly Trp Pro
        115                 120                 125

Arg Glu Arg Cys Leu His Asn Leu Ile Cys Gln Glu Arg Asp Val Phe
    130                 135                 140

Leu Pro Gly His His Cys Ser Cys Leu Lys Glu Leu Pro Pro Asn Gly
145                 150                 155                 160

Pro Phe Cys Leu Leu Gln Glu Asp Val Thr Leu Asn Met Arg Val Arg
                165                 170                 175

Leu Asn Val Gly Phe Gln Glu Asp Leu Met Asn Thr Ser Ser Ala Leu
            180                 185                 190

Tyr Arg Ser Tyr Lys Thr Asp Leu Glu Thr Ala Arg Lys Gly Tyr Gly
        195                 200                 205

Ile Leu Pro Gly Phe Lys Gly Val Thr Val Thr Gly Phe Lys Ser Gly
    210                 215                 220

Ser Val Val Val Thr Tyr Glu Val Lys Thr Thr Pro Pro Ser Leu Glu
225                 230                 235                 240

Leu Ile His Lys Ala Asn Glu Gln Val Val Gln Ser Leu Asn Gln Thr
                245                 250                 255
```

-continued

```
Tyr Lys Met Asp Tyr Asn Ser Phe Gln Ala Val Thr Ile Asn Glu Ser
            260                 265                 270

Asn Phe Phe Val Thr Pro Glu Ile Ile Phe Glu Gly Asp Thr Val Ser
        275                 280                 285

Leu Val Cys Glu Lys Glu Val Leu Ser Ser Asn Val Ser Trp Arg Tyr
    290                 295                 300

Glu Glu Gln Gln Leu Glu Ile Gln Asn Ser Ser Arg Phe Ser Ile Tyr
305                 310                 315                 320

Thr Ala Leu Phe Asn Asn Met Thr Ser Val Ser Lys Leu Thr Ile His
                325                 330                 335

Asn Ile Thr Pro Gly Asp Ala Gly Glu Tyr Val Cys Lys Leu Ile Leu
            340                 345                 350

Asp Ile Phe Glu Tyr Glu Cys Lys Lys Lys Ile Asp Val Met Pro Ile
        355                 360                 365

Gln Ile Leu Ala Asn Glu Glu Met Lys Val Met Cys Asp Asn Asn Pro
    370                 375                 380

Val Ser Leu Asn Cys Cys Ser Gln Gly Asn Val Asn Trp Ser Lys Val
385                 390                 395                 400

Glu Trp Lys Gln Glu Gly Lys Ile Asn Ile Pro Gly Thr Pro Glu Thr
                405                 410                 415

Asp Ile Asp Ser Ser Cys Ser Arg Tyr Thr Leu Lys Ala Asp Gly Thr
            420                 425                 430

Gln Cys Pro Ser Gly Ser Ser Gly Thr Thr Val Ile Tyr Thr Cys Glu
        435                 440                 445

Phe Ile Ser Ala Tyr Gly Ala Arg Gly Ser Ala Asn Ile Lys Val Thr
    450                 455                 460

Phe Ile Ser Val Ala Asn Leu Thr Ile Thr Pro Asp Pro Ile Ser Val
465                 470                 475                 480

Ser Glu Gly Gln Asn Phe Ser Ile Lys Cys Ile Ser Asp Val Ser Asn
                485                 490                 495

Tyr Asp Glu Val Tyr Trp Asn Thr Ser Ala Gly Ile Lys Ile Tyr Gln
            500                 505                 510

Arg Phe Tyr Thr Thr Arg Arg Tyr Leu Asp Gly Ala Glu Ser Val Leu
        515                 520                 525

Thr Val Lys Thr Ser Thr Arg Glu Trp Asn Gly Thr Tyr His Cys Ile
    530                 535                 540

Phe Arg Tyr Lys Asn Ser Tyr Ser Ile Ala Thr Lys Asp Val Ile Val
545                 550                 555                 560

His Pro Leu Pro Leu Lys Leu Asn Ile Met Val Asp Pro Leu Glu Ala
                565                 570                 575

Thr Val Ser Cys Ser Gly Ser His His Ile Lys Cys Cys Ile Glu Glu
            580                 585                 590

Asp Gly Asp Tyr Lys Val Thr Phe His Thr Gly Ser Ser Ser Leu Pro
        595                 600                 605

Ala Ala Lys Glu Val Asn Lys Lys Gln Val Cys Tyr Lys His Asn Phe
    610                 615                 620

Asn Ala Ser Ser Val Ser Trp Cys Ser Lys Thr Val Asp Val Cys Cys
625                 630                 635                 640

His Phe Thr Asn Ala Ala Asn Asn Ser Val Trp Ser Pro Ser Met Lys
                645                 650                 655

Leu Asn Leu Val Pro Gly Glu Asn Ile Thr Cys Gln Asp Pro Val Ile
            660                 665                 670
```

-continued

```
Gly Val Gly Glu Pro Gly Lys Val Ile Gln Lys Leu Cys Arg Phe Ser
        675                 680                 685

Asn Val Pro Ser Ser Pro Glu Ser Pro Ile Gly Gly Thr Ile Thr Tyr
    690                 695                 700

Lys Cys Val Gly Ser Gln Trp Glu Glu Lys Arg Asn Asp Cys Ile Ser
705                 710                 715                 720

Ala Pro Ile Asn Ser Leu Leu Gln Met Ala Lys Leu Ile Lys Ser Pro
                725                 730                 735

Ser Gln Asp Glu Met Leu Pro Thr Tyr Leu Lys Asp Leu Ser Ile Ser
            740                 745                 750

Ile Asp Lys Ala Glu His Glu Ile Ser Ser Ser Pro Gly Ser Leu Gly
        755                 760                 765

Ala Ile Ile Asn Ile Leu Asp Leu Leu Ser Thr Val Pro Thr Gln Val
    770                 775                 780

Asn Ser Glu Met Met Thr Val Leu Ser Thr Val Asn Val Ile Leu Gly
785                 790                 795                 800

Lys Pro Val Leu Asn Thr Trp Lys Val Leu Gln Gln Gln Trp Thr Asn
                805                 810                 815

Gln Ser Ser Gln Leu Leu His Ser Val Glu Arg Phe Ser Gln Ala Leu
            820                 825                 830

Gln Ser Gly Asp Ser Pro Pro Leu Ser Phe Ser Gln Thr Asn Val Gln
        835                 840                 845

Met Ser Ser Met Val Ile Lys Ser Ser His Pro Glu Thr Tyr Gln Gln
    850                 855                 860

Arg Phe Val Phe Pro Tyr Phe Asp Leu Trp Gly Asn Val Val Ile Asp
865                 870                 875                 880

Lys Ser Tyr Leu Glu Asn Leu Gln Ser Asp Ser Ser Ile Val Thr Met
                885                 890                 895

Ala Phe Pro Thr Leu Gln Ala Ile Leu Ala Gln Asp Ile Gln Glu Asn
            900                 905                 910

Asn Phe Ala Glu Ser Leu Val Met Thr Thr Thr Val Ser His Asn Thr
        915                 920                 925

Thr Met Pro Phe Arg Ile Ser Met Thr Phe Lys Asn Asn Ser Pro Ser
    930                 935                 940

Gly Gly Glu Thr Lys Cys Val Phe Trp Asn Phe Arg Leu Ala Asn Asn
945                 950                 955                 960

Thr Gly Gly Trp Asp Ser Ser Gly Cys Tyr Val Glu Glu Gly Asp Gly
                965                 970                 975

Asp Asn Val Thr Cys Ile Cys Asp His Leu Thr Ser Phe Ser Ile Leu
            980                 985                 990

Met Ser Pro Asp Ser Pro Asp Pro  Ser Ser Leu Leu Gly  Ile Leu Leu
        995                 1000                1005

Asp Ile  Ile Ser Tyr Val Gly  Val Gly Phe Ser Ile  Leu Ser Leu
    1010                1015                1020

Ala Ala  Cys Leu Val Val Glu  Ala Val Val Trp Lys  Ser Val Thr
    1025                1030                1035

Lys Asn  Arg Thr Ser Tyr Met  Arg His Thr Cys Ile  Val Asn Ile
    1040                1045                1050

Ala Ala  Ser Leu Leu Val Ala  Asn Thr Trp Phe Ile  Val Val Ala
    1055                1060                1065

Ala Ile  Gln Asp Asn Arg Tyr  Ile Leu Cys Lys Thr  Ala Cys Val
    1070                1075                1080

Ala Ala  Thr Phe Phe Ile His  Phe Phe Tyr Leu Ser  Val Phe Phe
```

-continued

```
    1085                1090                1095

Trp Met  Leu Thr Leu Gly Leu  Met Leu Phe Tyr Arg  Leu Val Phe
    1100                1105                1110

Ile Leu  His Glu Thr Ser Arg  Ser Thr Gln Lys Ala  Ile Ala Phe
    1115                1120                1125

Cys Leu  Gly Tyr Gly Cys Pro  Leu Ala Ile Ser Val  Ile Thr Leu
    1130                1135                1140

Gly Ala  Thr Gln Pro Arg Glu  Val Tyr Thr Arg Lys  Asn Val Cys
    1145                1150                1155

Trp Leu  Asn Trp Glu Asp Thr  Lys Ala Leu Leu Ala  Phe Ala Ile
    1160                1165                1170

Pro Ala  Leu Ile Ile Val Val  Val Asn Ile Thr Ile  Thr Ile Val
    1175                1180                1185

Val Ile  Thr Lys Ile Leu Arg  Pro Ser Ile Gly Asp  Lys Pro Cys
    1190                1195                1200

Lys Gln  Glu Lys Ser Ser Leu  Phe Gln Ile Ser Lys  Ser Ile Gly
    1205                1210                1215

Val Leu  Thr Pro Leu Leu Gly  Leu Thr Trp Gly Phe  Gly Leu Thr
    1220                1225                1230

Thr Val  Phe Pro Gly Thr Asn  Leu Val Phe His Ile  Ile Phe Ala
    1235                1240                1245

Ile Leu  Asn Val Phe Gln Leu  Phe Ile Leu Leu Phe  Gly Cys Leu
    1250                1255                1260

Trp Asp  Leu Lys Gln Glu Ala  Leu Leu Asn Lys Phe  Ser Leu Ser
    1265                1270                1275

Arg Trp  Ser Ser Gln His Ser  Lys Thr Ser Leu Gly  Ser Ser Thr
    1280                1285                1290

Pro Val  Phe Ser Met Ser Ser  Pro Ile Ser Arg Arg  Phe Asn Asn
    1295                1300                1305

Leu Phe  Gly Lys Thr Gly Thr  Tyr Asn Val Ser Thr  Pro Glu Ala
    1310                1315                1320

Thr Ser  Ser Ser Leu Glu Asn  Ser Ser Ser Ala Ser  Ser Leu Leu
    1325                1330                1335

Asn


<210> SEQ ID NO 14
<211> LENGTH: 4038
<212> TYPE: DNA
<213> ORGANISM: Artificial Sequence
<220> FEATURE:
<223> OTHER INFORMATION: Synthetic Organism

<400> SEQUENCE: 14

atgaaatccc caaggagaac cactttgtgc ctcatgttta ttgtgattta ttcttccaaa     60

gctgcactga actggaatta cgagtctact attcatcctt tgagtcttca tgaacatgaa    120

ccagctggtg aagaggcact gaggcaaaaa cgagccgttg ccacaaaaag tcctacggct    180

gaagaataca ctgttaatat tgagatcagt tttgaaaatg catccttcct ggatcctatc    240

aaagcctact tgaacagcct cagttttcca attcatggga ataacactga ccaaattacc    300

gacattttga gcataaatgt gacaacagtc tgcagacctg ctggaaatga aatctggtgc    360

tcctgcgaga caggttatgg gtggcctcgg gaaaggtgtc ttcacaatct catttgtcaa    420

gagcgtgacg tcttcctccc agggcaccat tgcagttgcc ttaaagaact gcctcccaat    480

ggaccttttt gcctgcttca ggaagatgtt accctgaaca tgagagtcag actaaatgta    540
```

-continued

```
ggctttcaag aagacctcat gaacacttcc tccgccctct ataggtccta caagaccgac    600
ttggaaacag cgttccggaa gggttacgga attttaccag gcttcaaggg cgtgactgtg    660
acagggttca agtctggaag tgtggttgtg acatatgaag tcaagactac accaccatca    720
cttgagttaa tacataaagc caatgaacaa gttgtacaga gcctcaatca gacctacaaa    780
atggactaca actcctttca agcagttact atcaatgaaa gcaatttctt tgtcacacca    840
gaaatcatct ttgaagggga cacagtcagt ctggtgtgtg aaaaggaagt tttgtcctcc    900
aatgtgtctt ggcgctatga agaacagcag ttggaaatcc agaacagcag cagattctcg    960
atttacaccg cacttttcaa caacatgact tcggtgtcca agctcaccat ccacaacatc   1020
actccaggtg atgcaggtga atatgtttgc aaactgatat tagacatttt tgaatatgag   1080
tgcaagaaga aaatagatgt tatgcccatc caaattttgg caaatgaaga aatgaaggtg   1140
atgtgcgaca acaatcctgt atctttgaac tgctgcagtc agggtaatgt taattggagc   1200
aaagtagaat ggaagcagga aggaaaaata aatattccag gaacccctga gacagacata   1260
gattctagct gcagcagata caccctcaag gctgatggaa cccagtgccc aagcgggtcg   1320
tctggaacaa cagtcatcta cacttgtgag ttcatcagtg cctatggagc cagaggcagt   1380
gcaaacataa aagtgacatt catctctgtg gccaatctaa caataacccc ggacccaatt   1440
tctgtttctg agggacaaaa cttttctata aaatgcatca gtgatgtgag taactatgat   1500
gaggtttatt ggaacacttc tgctggaatt aaaatatacc aaagatttta taccacgagg   1560
aggtatcttg atggagcaga atcagtactg acagtcaaga cctcgaccag ggagtggaat   1620
ggaacctatc actgcatatt tagatataag aattcataca gtattgcaac caaagacgtc   1680
attgttcacc cgctgcctct aaagctgaac atcatggttg atcctttgga agctactgtt   1740
tcatgcagtg gttcccatca catcaagtgc tgcatagagg aggatggaga ctacaaagtt   1800
actttccata cgggttcctc atcccttcct gctgcaaaag aagttaacaa aaaacaagtg   1860
tgctacaaac acaatttcaa tgcaagctca gtttcctggt gttcaaaaac tgttgatgtg   1920
tgttgtcact ttaccaatgc tgctaataat tcagtctgga gcccatctat gaagctgaat   1980
ctggttcctg gggaaaacat cacatgccag gatcccgtaa taggtgtcgg agagccgggg   2040
aaagtcatcc agaagctatg ccggttctca aacgttccca gcagccctga gagtcccatt   2100
ggcgggacca tcacttacaa atgtgtaggc tcccagtggg aggagaagag aaatgactgc   2160
atctctgccc caataaacag tctgctccag atggctaagg ctttgatcaa gagcccctct   2220
caggatgaga tgctccctac atacctgaag gatctttcta ttagcataga caaagcggaa   2280
catgaaatca gctcttctcc tgggagtctg ggagccatta ttaacatcct tgatctgctc   2340
tcaacagttc caacccaagt aaattcagaa atgatgacgc acgtgctctc tacggttaat   2400
gtcatccttg gcaagcccgt cttgaacacc tggaaggttt tacaacagca atggaccaat   2460
cagagttcac agctactaca ttcagtggaa agattttccc aagcattaca gtcgggagat   2520
agccctcctt tgtccttctc ccaaactaat gtgcagatga gcagcatggt aatcaagtcc   2580
agccacccag aaacctatca acagaggttt gttttcccat actttgacct ctggggcaat   2640
gtggtcattg acaagagcta tctagaaaac ttgcagtcgg attcgtctat tgtcaccatg   2700
gctttcccaa ctctccaagc catccttgcc caggatatcc aggaaaataa ctttgcagag   2760
agcttagtga tgacaaccac tgtcagccac aatacaacta tgccattcag gatttcaatg   2820
acttttaaga acaatagccc ttcaggcggc gaaacgaagt gtgtcttctg gaacttcagg   2880
```

-continued

```
cttgccaaca acacaggggg gtgggacagc agtgggtgct atgtagaaga aggtgatggg   2940

gacaatgtca cctgtatctg tgaccaccta acatcattct ccatcctcat gtcccctgac   3000

tccccagatc ctagttctct cctgggaata ctcctggata ttatttctta tgttggggtg   3060

ggcttttcca tcttgagctt ggcagcctgt ctagttgtgg aagctgtggt gtggaaatcg   3120

gtgaccaaga accggacttc ttatatgcgc cacacctgca tagtgaatat cgctgcctcc   3180

cttctggtcg ccaacacctg gttcattgtg gtcgctgcca tccaggacaa tcgctacata   3240

ctctgcaaga cagcctgtgt ggctgccacc ttcttcatcc acttcttcta cctcagcgtc   3300

ttcttctgga tgctgacact gggcctcatg ctgttctatc gcctggtttt cattctgcat   3360

gaaacaagca ggtccactca gaaagccatt gccttctgtc ttggctatgg ctgcccactt   3420

gccatctcgg tcatcacgct gggagccacc cagccccggg aagtctatac gaggaagaat   3480

gtctgttggc tcaactggga ggacaccaag gccctgctgg ctttcgccat cccagcactg   3540

atcattgtgg tggtgaacat aaccatcact attgtggtca tcaccaagat cctgaggcct   3600

tccattggag acaagccatg caagcaggag aagagcagcc tgtttcagat cagcaagagc   3660

attggggtcc tcacaccact cttgggcctc acttggggtt ttggtctcac cactgtgttc   3720

ccagggacca accttgtgtt ccatatcata tttgccatcc tcaatgtctt ccagggatta   3780

ttcattttac tctttggatg cctctgggat ctgaaggtac aggaagcttt gctgaataag   3840

ttttcattgt cgagatggtc ttcacagcac tcaaagtcaa catccctggg ttcatccaca   3900

cctgtgtttt ctatgagttc tccaatatca aggagattta acaatttgtt tggtaaaaca   3960

ggaacgtata atgtttccac cccagaagca accagctcat ccctggaaaa ctcatccagt   4020

gcttcttcgt tgctcaac                                                 4038
```

```
<210> SEQ ID NO 15
<211> LENGTH: 460
<212> TYPE: PRT
<213> ORGANISM: Artificial Sequence
<220> FEATURE:
<223> OTHER INFORMATION: Synthetic Organism

<400> SEQUENCE: 15

Ile Leu Asn Ser Lys Ser Ile Ser Asn Trp Thr Phe Ile Arg Asp Arg
1               5                   10                  15

Asn Ser Ser Tyr Ile Leu Leu His Ser Val Asn Ser Phe Ala Arg Arg
            20                  25                  30

Leu Phe Ile Asp Asn Ile Pro Val Asp Ile Ser Asp Val Phe Ile His
        35                  40                  45

Thr Met Gly Thr Thr Ile Ser Gly Asp Asn Ile Gly Lys Asn Phe Thr
    50                  55                  60

Phe Ser Met Arg Ile Asn Asp Thr Ser Asn Glu Val Thr Gly Arg Val
65                  70                  75                  80

Leu Ile Ser Arg Asp Glu Leu Arg Lys Val Pro Ser Pro Ser Gln Val
                85                  90                  95

Ile Ser Ile Ala Phe Pro Thr Ile Gly Ala Ile Leu Glu Ala Ser Leu
            100                 105                 110

Leu Glu Asn Val Thr Val Asn Gly Leu Val Leu Ser Ala Ile Leu Pro
        115                 120                 125

Lys Glu Leu Lys Arg Ile Ser Leu Ile Phe Glu Lys Ile Ser Lys Ser
    130                 135                 140

Glu Glu Arg Arg Thr Gln Cys Val Gly Trp His Ser Val Glu Asn Arg
145                 150                 155                 160
```

-continued

```
Trp Asp Gln Gln Ala Cys Lys Met Ile Gln Glu Asn Ser Gln Gln Ala
                165                 170                 175

Val Cys Lys Cys Arg Pro Ser Lys Leu Phe Thr Ser Phe Ser Ile Leu
            180                 185                 190

Met Ser Pro His Ile Leu Glu Ser Leu Ile Leu Thr Tyr Ile Thr Tyr
        195                 200                 205

Val Gly Leu Gly Ile Ser Ile Cys Ser Leu Ile Leu Cys Leu Ser Ile
    210                 215                 220

Glu Val Leu Val Trp Ser Gln Val Thr Lys Thr Glu Ile Thr Tyr Leu
225                 230                 235                 240

Arg His Val Cys Ile Val Asn Ile Ala Ala Thr Leu Leu Met Ala Asp
                245                 250                 255

Val Trp Phe Ile Val Ala Ser Phe Leu Ser Gly Pro Ile Thr His His
            260                 265                 270

Lys Gly Cys Val Ala Ala Thr Phe Phe Val His Phe Phe Tyr Leu Ser
        275                 280                 285

Val Phe Phe Trp Met Leu Ala Lys Ala Leu Leu Ile Leu Tyr Gly Ile
    290                 295                 300

Met Ile Val Phe His Thr Leu Pro Lys Ser Val Leu Val Ala Ser Leu
305                 310                 315                 320

Phe Ser Val Gly Tyr Gly Cys Pro Leu Ala Ile Ala Ala Ile Thr Val
                325                 330                 335

Ala Ala Thr Glu Pro Gly Lys Gly Tyr Leu Arg Pro Glu Ile Cys Trp
            340                 345                 350

Leu Asn Trp Asp Met Thr Lys Ala Leu Leu Ala Phe Val Ile Pro Ala
        355                 360                 365

Leu Ala Ile Val Val Val Asn Leu Ile Thr Val Thr Leu Val Ile Val
    370                 375                 380

Lys Thr Gln Arg Ala Ala Ile Gly Asn Ser Met Phe Gln Glu Val Arg
385                 390                 395                 400

Ala Ile Val Arg Ile Ser Lys Asn Ile Ala Ile Leu Thr Pro Leu Leu
                405                 410                 415

Gly Leu Thr Trp Gly Phe Gly Val Ala Thr Val Ile Asp Asp Arg Ser
            420                 425                 430

Leu Ala Phe His Ile Ile Phe Ser Leu Leu Asn Ala Phe Gln Phe Phe
        435                 440                 445

Ile Leu Val Phe Gly Thr Ile Leu Asp Pro Lys Val
    450                 455                 460
```

<210> SEQ ID NO 16
<211> LENGTH: 1383
<212> TYPE: DNA
<213> ORGANISM: Artificial Sequence
<220> FEATURE:
<223> OTHER INFORMATION: Synthetic Organism

<400> SEQUENCE: 16

```
attcttaaca gcaaaagcat ctccaactgg actttcattc gtgacagaaa cagcagctat     60

atcctgctac attcagtcaa ctcctttgca agaaggctat tcatagataa catccctgtt    120

gacatatcag atgtcttcat tcatactatg ggcaccacca tatctggaga taacattgga    180

aaaaatttca ctttttctat gagaattaat gacaccagca atgaagtcac tgggagagtg    240

ttgatcagca gagatgaact tcggaaggtg ccttcccctt ctcaggtcat cagcattgca    300

tttccaacta ttggggctat tttggaagcc agtcttttgg aaaatgttac tgtaaatggg    360
```

-continued

```
cttgtcctgt ctgccatttt gcccaaggaa cttaaaagaa tctcactgat ttttgaaaag    420

atcagcaagt cagaggagag gaggacacag tgtgttggct ggcactctgt ggagaacaga    480

tgggaccagc aggcctgcaa aatgattcaa gaaaactccc agcaagctgt ttgcaaatgt    540

aggccaagca aattgtttac ctctttctca attcttatgt cacctcacat cttagagagt    600

ctgattctga cttacatcac atatgtaggc ctgggcattt ctatttgcag cctgatcctt    660

tgcttgtcca ttgaggtcct agtctggagc caagtgacaa agacagagat cacctattta    720

cgccatgtgt gcattgttaa cattgcagcc actttgctga tggcagatgt gtggttcatt    780

gtggcttcct ttcttagtgg cccaataaca caccacaagg gatgtgtggc agccacattt    840

tttgttcatt tcttttacct ttctgtattt ttctggatgc ttgccaaggc actccttatc    900

ctctatggaa tcatgattgt tttccatacc ttgcccaagt cagtcctggt ggcatctctg    960

ttttcagtgg gctatggatg ccctttggcc attgctgcca tcactgttgc tgccactgaa   1020

cctggcaaag gctatctacg acctgagatc tgctggctca actgggacat gaccaaagcc   1080

ctcctggcct tcgtgatccc agctttggcc atcgtggtag taaacctgat cacagtcaca   1140

ctggtgattg tcaagaccca gcgagctgcc attggcaatt ccatgttcca ggaagtgaga   1200

gccattgtga gaatcagcaa gaacatcgcc atcctcacac cacttctggg actgacctgg   1260

ggatttggag tagccactgt catcgatgac agatccctgg ccttccacat tatcttctcc   1320

ctgctcaatg cattccaggg tttcttcatc ctagtgtttg gaaccatcct ggatccaaag   1380

gta                                                                 1383
```

<210> SEQ ID NO 17
<211> LENGTH: 299
<212> TYPE: PRT
<213> ORGANISM: Artificial Sequence
<220> FEATURE:
<223> OTHER INFORMATION: Synthetic Organism

<400> SEQUENCE: 17

```
Gly Thr Thr Gly Asp Trp Ser Ser Glu Gly Cys Ser Thr Glu Val Arg
1               5                   10                  15

Pro Glu Gly Thr Val Cys Cys Cys Asp His Leu Thr Phe Phe Ala Leu
            20                  25                  30

Leu Leu Pro Thr Leu Asp Gln Ser Thr Val His Ile Leu Thr Arg Ile
        35                  40                  45

Ser Gln Ala Gly Cys Gly Val Ser Met Ile Phe Leu Ala Phe Thr Ile
    50                  55                  60

Ile Leu Tyr Ala Phe Leu Arg Leu Ser Arg Glu Arg Phe Lys Ser Glu
65                  70                  75                  80

Asp Ala Pro Lys Ile His Val Ala Leu Gly Gly Ser Leu Phe Leu Leu
                85                  90                  95

Asn Leu Ala Phe Leu Val Asn Val Gly Ser Gly Ser Lys Gly Ser Asp
            100                 105                 110

Ala Ala Cys Trp Ala Arg Gly Ala Val Phe His Tyr Phe Leu Leu Cys
        115                 120                 125

Ala Phe Thr Trp Met Gly Leu Glu Ala Phe His Leu Tyr Leu Leu Ala
    130                 135                 140

Val Arg Val Phe Asn Thr Tyr Phe Gly His Tyr Phe Leu Lys Leu Ser
145                 150                 155                 160

Leu Val Gly Trp Gly Leu Pro Ala Leu Met Val Ile Gly Thr Gly Ser
                165                 170                 175
```

-continued

```
Ala Asn Ser Tyr Gly Leu Tyr Thr Ile Arg Asp Arg Glu Asn Arg Thr
            180                 185                 190

Ser Leu Glu Leu Cys Trp Phe Arg Glu Gly Thr Thr Met Tyr Ala Leu
        195                 200                 205

Tyr Ile Thr Val His Gly Tyr Phe Leu Ile Thr Phe Leu Phe Gly Met
    210                 215                 220

Val Val Leu Ala Leu Val Val Trp Lys Ile Phe Thr Leu Ser Arg Ala
225                 230                 235                 240

Thr Ala Val Lys Glu Arg Gly Lys Asn Arg Lys Lys Val Leu Thr Leu
                245                 250                 255

Leu Gly Leu Ser Ser Leu Val Gly Val Thr Trp Gly Leu Ala Ile Phe
            260                 265                 270

Thr Pro Leu Gly Leu Ser Thr Val Tyr Ile Phe Ala Leu Phe Asn Ser
        275                 280                 285

Leu Gln Val Asp Phe Tyr Ile Leu Ile Phe Tyr
    290                 295


<210> SEQ ID NO 18
<211> LENGTH: 900
<212> TYPE: DNA
<213> ORGANISM: Artificial Sequence
<220> FEATURE:
<223> OTHER INFORMATION: Synthetic Organism

<400> SEQUENCE: 18

gggaccactg gagactggtc ttctgagggc tgctccacgg aggtcagacc tgaggggacc     60

gtgtgctgct gtgaccacct gaccttttc gccctgctcc tgagacccac cttggaccag    120

tccacggtgc atatcctcac acgcatctcc caggcgggct gtggggtctc catgatcttc    180

ctggccttca ccattattct ttatgccttt ctgaggcttt cccgggagag gttcaagtca    240

gaagatgccc caaagatcca cgtggccctg ggtggcagcc tgttcctcct gaatctggcc    300

ttcttggtca atgtggggag tggctcaaag gggtctgatg ctgcctgctg ggcccggggg    360

gctgtcttcc actacttcct gctctgtgcc ttcacctgga tgggccttga agccttccac    420

ctctacctgc tcgctgtcag ggtcttcaac acctacttcg ggcactactt cctgaagctg    480

agcctggtgg gctggggcct gcccgccctg atggtcatcg gcactgggag tgccaacagc    540

tacggcctct acaccatccg tgatagggag aaccgcacct ctctggagct atgctggttc    600

cgtgaaggga caaccatgta cgccctctat atcaccgtcc acggctactt cctcatcacc    660

ttcctctttg gcatggtggt cctggccctg gtggtctgga agatcttcac cctgtcccgt    720

gctacagcgg tcaaggagcg ggggaagaac cggaagaagg tgctcaccct gctgggcctc    780

tcgagcctgg tgggtgtgac atgggggttg gccatcttca ccccgttggg cctctccacc    840

gtctacatct ttgcactttt caactccttg caagttgatt tttacatatt gatcttctat    900


<210> SEQ ID NO 19
<211> LENGTH: 468
<212> TYPE: PRT
<213> ORGANISM: Artificial Sequence
<220> FEATURE:
<223> OTHER INFORMATION: Synthetic Organism
<220> FEATURE:
<221> NAME/KEY: misc_feature
<222> LOCATION: (370)..(370)
<223> OTHER INFORMATION: Xaa can be any naturally occurring amino acid

<400> SEQUENCE: 19
```

-continued

```
Asn His Ile Leu Asp Thr Ala Ala Ile Ser Asn Trp Ala Phe Ile Pro
1               5                   10                  15

Asn Lys Asn Ala Ser Ser Asp Leu Leu Gln Ser Val Asn Leu Phe Ala
            20                  25                  30

Arg Gln Leu His Ile His Asn Asn Ser Glu Asn Ile Val Asn Glu Leu
        35                  40                  45

Phe Ile Gln Thr Lys Gly Phe His Ile Asn His Asn Thr Ser Glu Lys
    50                  55                  60

Ser Leu Asn Phe Ser Met Ser Met Asn Asn Thr Thr Glu Asp Ile Leu
65                  70                  75                  80

Gly Met Val Gln Ile Pro Arg Gln Glu Leu Arg Lys Leu Trp Pro Asn
                85                  90                  95

Ala Ser Gln Ala Ile Ser Ile Ala Phe Pro Thr Leu Gly Ala Ile Leu
            100                 105                 110

Arg Glu Ala His Leu Gln Asn Val Ser Leu Pro Arg Gln Val Asn Gly
        115                 120                 125

Leu Val Leu Ser Val Val Leu Pro Glu Arg Leu Gln Glu Ile Ile Leu
    130                 135                 140

Thr Phe Glu Lys Ile Asn Lys Thr Arg Asn Ala Arg Ala Gln Cys Val
145                 150                 155                 160

Gly Trp His Ser Lys Lys Arg Arg Trp Asp Glu Lys Ala Cys Gln Met
                165                 170                 175

Met Leu Asp Ile Arg Asn Glu Val Lys Cys Arg Cys Asn Tyr Thr Ser
            180                 185                 190

Val Val Met Ser Phe Ser Ile Leu Met Ser Ser Lys Ser Met Thr Asp
        195                 200                 205

Lys Val Leu Asp Tyr Ile Thr Cys Ile Gly Leu Ser Val Ser Ile Leu
    210                 215                 220

Ser Leu Val Leu Cys Leu Ile Ile Glu Ala Thr Val Trp Ser Arg Val
225                 230                 235                 240

Val Val Thr Glu Ile Ser Tyr Met Arg His Val Cys Ile Val Asn Ile
                245                 250                 255

Ala Val Ser Leu Leu Thr Ala Asn Val Trp Phe Ile Ile Gly Ser His
            260                 265                 270

Phe Asn Ile Lys Ala Gln Asp Tyr Asn Met Cys Val Ala Val Thr Phe
        275                 280                 285

Phe Ser His Phe Phe Tyr Leu Ser Leu Phe Phe Trp Met Leu Phe Lys
    290                 295                 300

Ala Leu Leu Ile Ile Tyr Gly Ile Leu Val Ile Phe Arg Arg Met Met
305                 310                 315                 320

Lys Ser Arg Met Met Val Ile Gly Phe Ala Ile Gly Tyr Gly Cys Pro
                325                 330                 335

Leu Ile Ile Ala Val Thr Thr Val Ala Ile Thr Glu Pro Glu Lys Gly
            340                 345                 350

Tyr Ile Arg Pro Glu Ala Cys Trp Leu Asn Trp Asp Asn Thr Lys Ala
        355                 360                 365

Leu Xaa Ala Phe Ala Ile Pro Ala Phe Val Ile Val Ala Val Asn Leu
    370                 375                 380

Ile Val Val Leu Val Val Ala Val Asn Thr Gln Arg Pro Ser Ile Gly
385                 390                 395                 400

Ser Ser Lys Ser Gln Asp Val Val Ile Ile Met Arg Ile Ser Lys Asn
                405                 410                 415

Val Ala Ile Leu Thr Pro Leu Leu Gly Leu Thr Trp Gly Phe Gly Ile
```

-continued

```
            420                 425                 430

Ala Thr Leu Ile Glu Gly Thr Ser Leu Thr Phe His Ile Ile Phe Ala
        435                 440                 445

Leu Leu Asn Ala Phe Gln Phe Phe Ile Leu Leu Phe Gly Thr Ile Met
    450                 455                 460

Asp His Lys Val
465


<210> SEQ ID NO 20
<211> LENGTH: 1407
<212> TYPE: DNA
<213> ORGANISM: Artificial Sequence
<220> FEATURE:
<223> OTHER INFORMATION: Synthetic Organism

<400> SEQUENCE: 20

aaccacatcc tcgacacagc agccatttca aactgggctt tcattcccaa caaaaatgcc     60

agctcggatt tgttgcagtc agtgaatttg tttgccagac aactccacat ccacaataat    120

tctgagaaca ttgtgaatga actcttcatt cagacaaaag ggtttcacat caaccataat    180

acctcagaga aaagcctcaa tttctccatg agcatgaaca ataccacaga agatatctta    240

ggaatggtac agattcccag gcaagagcta aggaagctgt ggccaaatgc atcccaagcc    300

attagcatag ctttcccaac cttgggggct atcctgagag aagcccactt gcaaaatgtg    360

agtcttccca gacaggtaaa tggtctggtg ctatcagtgg ttttaccaga aaggttgcaa    420

gaaatcatac tcaccttcga aaagatcaat aaaacccgca atgccagagc ccagtgtgtt    480

ggctggcact ccaagaaaag gagatgggat gagaaagcgt gccaaatgat gttggatatc    540

aggaacgaag tgaaatgccg ctgtaactac accagtgtgg tgatgtcttt ttccattctc    600

atgtcctcca aatcgatgac cgacaaagtt ctggactaca tcacctgcat tgggctcagc    660

gtctcaatcc taagcttggt tctttgcctg atcattgaag ccacagtgtg gtcccgggtg    720

gttgtgacgg agatatcata catgcgtcac gtgtgcatcg tgaatatagc agtgtccctt    780

ctgactgcca atgtgtggtt tatcataggc tctcacttta acattaaggc ccaggactac    840

aacatgtgtg ttgcagtgac atttttcagc cactttttct acctctctct gtttttctgg    900

atgctcttca aagcattgct catcatttat ggaatattgg tcattttccg taggatgatg    960

aagtcccgaa tgatggtcat tggctttgcc attggctatg ggtgcccatt gatcattgct   1020

gtcactacag ttgctatcac agagccagag aaaggctaca taagacctga ggcctgttgg   1080

cttaactggg acaataccaa agccctttaa gcatttgcca tcccggcgtt cgtcattgtg   1140

gctgtaaatc tgattgtggt tttggttgtt gctgtcaaca ctcagaggcc ctctattggc   1200

agttccaagt ctcaggatgt ggtcataatt atgaggatca gcaaaaatgt tgccatcctc   1260

actccactgc tgggactgac ctggggtttt ggaatagcca ctctcataga aggcacttcc   1320

ttgacgttcc atataatttt tgccttgctc aatgctttcc agggtttttt catcctgctg   1380

tttggaacca ttatggatca caaggta                                       1407
```

We claim:

1. An isolated polynucleotide comprising the nucleic acid sequence of FIG. 1B.

* * * * *